United States Patent
Braido et al.

(10) Patent No.: US 12,390,327 B2
(45) Date of Patent: Aug. 19, 2025

(54) STATIONARY INTRA-ANNULAR HALO DESIGNS FOR PARAVALVULAR LEAK (PVL) REDUCTION—ACTIVE CHANNEL FILLING CUFF DESIGNS

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L. McCarthy, Vadnais Heights, MN (US); Mina S. Fahim, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 388 days.

(21) Appl. No.: 17/821,317

(22) Filed: Aug. 22, 2022

(65) Prior Publication Data
US 2022/0395368 A1 Dec. 15, 2022

Related U.S. Application Data

(60) Continuation of application No. 16/680,782, filed on Nov. 12, 2019, now Pat. No. 11,419,716, which is a
(Continued)

(51) Int. Cl.
*A61F 2/24* (2006.01)

(52) U.S. Cl.
CPC .......... *A61F 2/2403* (2013.01); *A61F 2/2418* (2013.01); *A61F 2210/0061* (2013.01); *A61F 2250/0069* (2013.01)

(58) Field of Classification Search
CPC ........ A61F 2/24; A61F 2/2418; A61F 2/2412; A61F 2250/0069
See application file for complete search history.

(56) References Cited

U.S. PATENT DOCUMENTS

| 3,657,744 A | 4/1972 | Ersek |
| 4,275,469 A | 6/1981 | Gabbay |
(Continued)

FOREIGN PATENT DOCUMENTS

| DE | 19857887 B4 | 5/2005 |
| DE | 10121210 B4 | 11/2005 |
(Continued)

OTHER PUBLICATIONS

"Transluminal Implantation of Artificial Heart Valves", Andersen, H. R., et al., European Heart Journal, vol. 13, No. 5, May 1992, pp. 704-708.
(Continued)

*Primary Examiner* — Christopher D. Prone
(74) *Attorney, Agent, or Firm* — SLEMAN & LUND LLP

(57) ABSTRACT

A prosthetic heart valve may include a collapsible and expandable stent extending in a flow direction between a proximal end and a distal end, a cuff attached to an annulus section of the stent and having an outer surface facing in a radial direction orthogonal to the flow direction, a plurality of prosthetic valve leaflets attached to the cuff, and a sealing structure attached to the annulus section of the stent at an inner edge of the sealing structure. The flow direction may be defined from the proximal end toward the distal end. The sealing structure may have an outer edge remote from the inner edge. The sealing structure may have a collapsed condition with the outer edge disposed adjacent the outer surface of the cuff and an expanded condition with the outer edge spaced apart from the outer surface of the cuff.

19 Claims, 6 Drawing Sheets

Related U.S. Application Data continuation of application No. 15/710,007, filed on Sep. 20, 2017, now Pat. No. 10,500,039, which is a division of application No. 14/601,810, filed on Jan. 21, 2015, now Pat. No. 9,820,852.

(60) Provisional application No. 61/931,265, filed on Jan. 24, 2014.

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,759,758 A | 7/1988 | Gabbay |
| 4,816,029 A | 3/1989 | Penny, III |
| 4,878,906 A | 11/1989 | Lindemann |
| 4,922,905 A | 5/1990 | Strecker |
| 4,994,077 A | 2/1991 | Dobben |
| 5,411,552 A | 5/1995 | Andersen |
| 5,415,664 A | 5/1995 | Pinchuk |
| 5,480,423 A | 1/1996 | Ravenscroft |
| 5,843,167 A | 12/1998 | Dwyer |
| 5,855,601 A | 1/1999 | Bessler |
| 5,924,424 A | 7/1999 | Stevens |
| 5,935,163 A | 8/1999 | Gabbay |
| 5,961,549 A | 10/1999 | Nguyen |
| 5,968,068 A | 10/1999 | Dehdashtian |
| 6,045,576 A | 4/2000 | Starr |
| 6,077,297 A | 6/2000 | Robinson |
| 6,083,257 A | 7/2000 | Taylor |
| 6,090,140 A | 7/2000 | Gabbay |
| 6,214,036 B1 | 4/2001 | Letendre |
| 6,264,691 B1 | 7/2001 | Gabbay |
| 6,267,783 B1 | 7/2001 | Letendre |
| 6,306,141 B1 | 10/2001 | Jervis |
| 6,368,348 B1 | 4/2002 | Gabbay |
| 6,419,695 B1 | 7/2002 | Gabbay |
| 6,458,153 B1 | 10/2002 | Bailey |
| 6,468,660 B2 | 10/2002 | Ogle |
| 6,488,702 B1 | 12/2002 | Besselink |
| 6,517,576 B2 | 2/2003 | Gabbay |
| 6,533,810 B2 | 3/2003 | Hankh |
| 6,582,464 B2 | 6/2003 | Gabbay |
| 6,610,088 B1 | 8/2003 | Gabbay |
| 6,623,518 B2 | 9/2003 | Thompson |
| 6,652,578 B2 | 11/2003 | Bailey |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser |
| 6,783,556 B1 | 8/2004 | Gabbay |
| 6,790,230 B2 | 9/2004 | Beyersdorf |
| 6,814,746 B2 | 11/2004 | Thompson |
| 6,830,584 B1 | 12/2004 | Seguin |
| 6,869,444 B2 | 3/2005 | Gabbay |
| 6,893,460 B2 | 5/2005 | Spenser |
| 6,908,481 B2 | 6/2005 | Cribier |
| 6,951,573 B1 | 10/2005 | Dilling |
| 7,018,406 B2 | 3/2006 | Seguin |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz |
| 7,247,167 B2 | 7/2007 | Gabbay |
| 7,267,686 B2 | 9/2007 | DiMatteo |
| 7,276,078 B2 | 10/2007 | Spenser |
| 7,311,730 B2 | 12/2007 | Gabbay |
| 7,320,704 B2 | 1/2008 | Lashinski |
| 7,329,278 B2 | 2/2008 | Seguin |
| 7,374,573 B2 | 5/2008 | Gabbay |
| 7,381,218 B2 | 6/2008 | Schreck |
| 7,381,219 B2 | 6/2008 | Salahieh |
| 7,452,371 B2 | 11/2008 | Pavcnik |
| 7,510,572 B2 | 3/2009 | Gabbay |
| 7,510,575 B2 | 3/2009 | Spenser |
| 7,524,331 B2 | 4/2009 | Birdsall |
| 7,534,261 B2 | 5/2009 | Friedman |
| RE40,816 E | 6/2009 | Taylor |
| 7,585,321 B2 | 9/2009 | Cribier |
| 7,628,805 B2 | 12/2009 | Spenser |
| 7,682,390 B2 | 3/2010 | Seguin |
| 7,708,775 B2 | 5/2010 | Rowe |
| 7,731,742 B2 | 6/2010 | Schlick |
| 7,748,389 B2 | 7/2010 | Salahieh |
| 7,780,725 B2 | 8/2010 | Haug |
| 7,799,069 B2 | 9/2010 | Bailey |
| 7,803,185 B2 | 9/2010 | Gabbay |
| 7,824,442 B2 | 11/2010 | Salahieh |
| 7,837,727 B2 | 11/2010 | Goetz |
| 7,846,203 B2 | 12/2010 | Cribier |
| 7,846,204 B2 | 12/2010 | Letac |
| 7,857,845 B2 | 12/2010 | Stacchino |
| 7,892,281 B2 | 2/2011 | Seguin |
| 7,914,569 B2 | 3/2011 | Nguyen |
| 7,959,666 B2 | 6/2011 | Salahieh |
| 7,959,672 B2 | 6/2011 | Salahieh |
| 7,972,378 B2 | 7/2011 | Tabor |
| 7,988,724 B2 | 8/2011 | Salahieh |
| 7,993,394 B2 | 8/2011 | Hariton |
| 8,016,877 B2 | 9/2011 | Seguin |
| D648,854 S | 11/2011 | Braido |
| 8,048,153 B2 | 11/2011 | Salahieh |
| 8,052,741 B2 | 11/2011 | Bruszewski |
| 8,052,749 B2 | 11/2011 | Salahieh |
| 8,052,750 B2 | 11/2011 | Tuval |
| 8,062,355 B2 | 11/2011 | Figulla |
| 8,075,611 B2 | 12/2011 | Millwee |
| D652,926 S | 1/2012 | Braido |
| D652,927 S | 1/2012 | Braido |
| D653,341 S | 1/2012 | Braido |
| D653,342 S | 1/2012 | Braido |
| D653,343 S | 1/2012 | Ness |
| D654,169 S | 2/2012 | Braido |
| D654,170 S | 2/2012 | Braido |
| 8,137,398 B2 | 3/2012 | Tuval |
| 8,142,497 B2 | 3/2012 | Friedman |
| D660,432 S | 5/2012 | Braido |
| D660,433 S | 5/2012 | Braido |
| D660,967 S | 5/2012 | Braido |
| 8,182,528 B2 | 5/2012 | Salahieh |
| 8,221,493 B2 | 7/2012 | Boyle |
| 8,230,717 B2 | 7/2012 | Matonick |
| 8,231,670 B2 | 7/2012 | Salahieh |
| 8,252,051 B2 | 8/2012 | Chau |
| 8,308,798 B2 | 11/2012 | Pintor |
| 8,313,525 B2 | 11/2012 | Tuval |
| 8,323,335 B2 | 12/2012 | Rowe |
| 8,323,336 B2 | 12/2012 | Hill |
| 8,343,213 B2 | 1/2013 | Salahieh |
| 8,348,995 B2 | 1/2013 | Tuval |
| 8,348,996 B2 | 1/2013 | Tuval |
| 8,348,998 B2 | 1/2013 | Pintor |
| 8,366,769 B2 | 2/2013 | Huynh |
| 8,403,983 B2 | 3/2013 | Quadri |
| 8,408,214 B2 | 4/2013 | Spenser |
| 8,414,643 B2 | 4/2013 | Tuval |
| 8,425,593 B2 | 4/2013 | Braido |
| 8,449,599 B2 | 5/2013 | Chau |
| 8,449,604 B2 | 5/2013 | Moaddeb |
| D684,692 S | 6/2013 | Braido |
| 8,454,686 B2 | 6/2013 | Alkhatib |
| 8,500,798 B2 | 8/2013 | Rowe |
| 8,568,474 B2 | 10/2013 | Yeung |
| 8,579,962 B2 | 11/2013 | Salahieh |
| 8,579,966 B2 | 11/2013 | Seguin |
| 8,585,755 B2 | 11/2013 | Chau |
| 8,591,575 B2 | 11/2013 | Cribier |
| 8,597,349 B2 | 12/2013 | Alkhatib |
| 8,603,159 B2 | 12/2013 | Seguin |
| 8,603,160 B2 | 12/2013 | Salahieh |
| 8,613,765 B2 | 12/2013 | Bonhoeffer |
| 8,623,074 B2 | 1/2014 | Ryan |
| 8,652,204 B2 | 2/2014 | Quill |
| 8,663,322 B2 | 3/2014 | Olli |

(56) References Cited

U.S. PATENT DOCUMENTS

| | | |
|---|---|---|
| 8,668,733 B2 | 3/2014 | Haug |
| 8,685,080 B2 | 4/2014 | White |
| 8,728,154 B2 | 5/2014 | Alkhatib |
| 8,747,459 B2 | 6/2014 | Nguyen |
| 8,764,820 B2 | 7/2014 | Dehdashtian |
| 8,795,357 B2 | 8/2014 | Yohanan |
| 8,801,776 B2 | 8/2014 | House |
| 8,808,356 B2 | 8/2014 | Braido |
| 8,828,078 B2 | 9/2014 | Salahieh |
| 8,834,563 B2 | 9/2014 | Righini |
| 8,840,661 B2 | 9/2014 | Manasse |
| 8,840,663 B2 | 9/2014 | Salahieh |
| 8,876,894 B2 | 11/2014 | Tuval |
| 8,876,895 B2 | 11/2014 | Tuval |
| 8,940,040 B2 | 1/2015 | Shahriari |
| 8,945,209 B2 | 2/2015 | Bonyuet |
| 8,961,595 B2 | 2/2015 | Alkhatib |
| 8,974,523 B2 | 3/2015 | Thill |
| 8,974,524 B2 | 3/2015 | Yeung |
| 9,326,856 B2 | 5/2016 | Schraut |
| 9,889,004 B2 | 2/2018 | Braido |
| 2002/0036220 A1 | 3/2002 | Gabbay |
| 2003/0014104 A1 | 1/2003 | Cribier |
| 2003/0023303 A1 | 1/2003 | Palmaz |
| 2003/0040792 A1 | 2/2003 | Gabbay |
| 2003/0050694 A1 | 3/2003 | Yang |
| 2003/0130726 A1 | 7/2003 | Thorpe |
| 2004/0049262 A1 | 3/2004 | Obermiller |
| 2004/0093075 A1 | 5/2004 | Kuehne |
| 2004/0111111 A1 | 6/2004 | Lin |
| 2004/0186563 A1 | 9/2004 | Lobbi |
| 2004/0210304 A1 | 10/2004 | Seguin |
| 2004/0260389 A1 | 12/2004 | Case |
| 2005/0075720 A1 | 4/2005 | Nguyen |
| 2005/0096726 A1 | 5/2005 | Sequin |
| 2005/0137682 A1 | 6/2005 | Justino |
| 2005/0137687 A1 | 6/2005 | Salahieh |
| 2005/0137695 A1 | 6/2005 | Salahieh |
| 2005/0137697 A1 | 6/2005 | Salahieh |
| 2005/0137701 A1 | 6/2005 | Salahieh |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad |
| 2006/0142848 A1 | 6/2006 | Gabbay |
| 2006/0149360 A1 | 7/2006 | Schwammenthal |
| 2006/0161249 A1 | 7/2006 | Realyvasquez |
| 2006/0167468 A1 | 7/2006 | Gabbay |
| 2006/0173532 A1 | 8/2006 | Flagle |
| 2006/0178740 A1 | 8/2006 | Stacchino |
| 2006/0195180 A1 | 8/2006 | Kheradvar |
| 2006/0206202 A1 | 9/2006 | Bonhoeffer |
| 2006/0241744 A1 | 10/2006 | Beith |
| 2006/0241745 A1 | 10/2006 | Solem |
| 2006/0259120 A1 | 11/2006 | Vongphakdy |
| 2006/0259136 A1 | 11/2006 | Nguyen |
| 2006/0259137 A1 | 11/2006 | Artof |
| 2006/0265056 A1 | 11/2006 | Nguyen |
| 2006/0276813 A1 | 12/2006 | Greenberg |
| 2006/0276874 A1 | 12/2006 | Wilson |
| 2006/0287717 A1 | 12/2006 | Rowe |
| 2007/0010876 A1 | 1/2007 | Salahieh |
| 2007/0016285 A1 | 1/2007 | Lane |
| 2007/0027534 A1 | 2/2007 | Bergheim |
| 2007/0043431 A1 | 2/2007 | Melsheimer |
| 2007/0043435 A1 | 2/2007 | Seguin |
| 2007/0055358 A1 | 3/2007 | Krolik |
| 2007/0067029 A1 | 3/2007 | Gabbay |
| 2007/0073387 A1 | 3/2007 | Forster |
| 2007/0073391 A1 | 3/2007 | Bourang |
| 2007/0088431 A1 | 4/2007 | Bourang |
| 2007/0093890 A1 | 4/2007 | Eliasen |
| 2007/0100435 A1 | 5/2007 | Case |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster |
| 2007/0213813 A1 | 9/2007 | Von Segesser |
| 2007/0233228 A1 | 10/2007 | Eberhardt |
| 2007/0239271 A1 | 10/2007 | Nguyen |
| 2007/0244545 A1 | 10/2007 | Birdsall |
| 2007/0244552 A1 | 10/2007 | Salahieh |
| 2007/0288087 A1 | 12/2007 | Fearnot |
| 2008/0021552 A1 | 1/2008 | Gabbay |
| 2008/0039934 A1 | 2/2008 | Styrc |
| 2008/0071369 A1 | 3/2008 | Tuval |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey |
| 2008/0140189 A1 | 6/2008 | Nguyen |
| 2008/0147182 A1 | 6/2008 | Righini |
| 2008/0147183 A1 | 6/2008 | Styrc |
| 2008/0154355 A1 | 6/2008 | Benichou |
| 2008/0154356 A1 | 6/2008 | Obermiller |
| 2008/0243245 A1 | 10/2008 | Thambar |
| 2008/0255662 A1 | 10/2008 | Stacchino |
| 2008/0262602 A1 | 10/2008 | Wilk |
| 2008/0269879 A1 | 10/2008 | Sathe |
| 2009/0054975 A1 | 2/2009 | Del Nido |
| 2009/0099653 A1* | 4/2009 | Suri ............... A61F 2/2418 623/2.11 |
| 2009/0112309 A1 | 4/2009 | Jaramillo |
| 2009/0138079 A1 | 5/2009 | Tuval |
| 2009/0276027 A1 | 11/2009 | Glynn |
| 2009/0276040 A1 | 11/2009 | Rowe |
| 2009/0287299 A1 | 11/2009 | Tabor |
| 2010/0004740 A1 | 1/2010 | Seguin |
| 2010/0036484 A1 | 2/2010 | Hariton |
| 2010/0049306 A1 | 2/2010 | House |
| 2010/0082094 A1 | 4/2010 | Quadri |
| 2010/0087907 A1 | 4/2010 | Lattouf |
| 2010/0131055 A1 | 5/2010 | Case |
| 2010/0168778 A1 | 7/2010 | Braido |
| 2010/0168839 A1 | 7/2010 | Braido |
| 2010/0168844 A1 | 7/2010 | Toomes |
| 2010/0185277 A1 | 7/2010 | Braido |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau |
| 2010/0234940 A1 | 9/2010 | Dolan |
| 2010/0249911 A1 | 9/2010 | Alkhatib |
| 2010/0249923 A1 | 9/2010 | Alkhatib |
| 2010/0286768 A1 | 11/2010 | Alkhatib |
| 2010/0298931 A1 | 11/2010 | Quadri |
| 2011/0029072 A1 | 2/2011 | Gabbay |
| 2011/0054466 A1 | 3/2011 | Rothstein |
| 2011/0098800 A1 | 4/2011 | Braido |
| 2011/0098802 A1 | 4/2011 | Braido |
| 2011/0137397 A1 | 6/2011 | Chau |
| 2011/0172765 A1 | 7/2011 | Nguyen |
| 2011/0208283 A1 | 8/2011 | Rust |
| 2011/0224678 A1 | 9/2011 | Gabbay |
| 2011/0238168 A1 | 9/2011 | Pellegrini |
| 2011/0264206 A1 | 10/2011 | Tabor |
| 2011/0295363 A1 | 12/2011 | Girard |
| 2012/0035722 A1 | 2/2012 | Tuval |
| 2012/0041550 A1 | 2/2012 | Salahieh |
| 2012/0053681 A1 | 3/2012 | Alkhatib |
| 2012/0071969 A1 | 3/2012 | Li |
| 2012/0078347 A1 | 3/2012 | Braido |
| 2012/0078350 A1 | 3/2012 | Wang |
| 2012/0101572 A1 | 4/2012 | Kovalsky |
| 2012/0123529 A1 | 5/2012 | Levi |
| 2012/0143324 A1 | 6/2012 | Rankin |
| 2012/0303116 A1 | 11/2012 | Gorman, III |
| 2013/0018458 A1 | 1/2013 | Yohanan |
| 2013/0274873 A1* | 10/2013 | Delaloye ............ A61F 2/2409 623/2.18 |

(56) References Cited

U.S. PATENT DOCUMENTS

| | | |
|---|---|---|
| 2013/0304200 A1 | 11/2013 | McLean |
| 2013/0331929 A1 | 12/2013 | Mitra |
| 2014/0005771 A1 | 1/2014 | Braido |
| 2014/0121763 A1 | 5/2014 | Duffy |
| 2014/0155997 A1 | 6/2014 | Braido |
| 2014/0214159 A1 | 7/2014 | Vidlund |
| 2014/0228946 A1 | 8/2014 | Chau |
| 2014/0303719 A1 | 10/2014 | Cox |
| 2014/0324164 A1 | 10/2014 | Gross |
| 2014/0343671 A1 | 11/2014 | Yohanan |
| 2014/0350668 A1 | 11/2014 | Delaloye |
| 2014/0350669 A1 | 11/2014 | Gillespie |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| EP | 2870946 A1 | 5/2015 |
| EP | 2898859 A1 | 7/2015 |
| EP | 2898859 B1 | 11/2018 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 0149213 A2 | 7/2001 |
| WO | 0156500 A2 | 8/2001 |
| WO | 2001054625 A1 | 8/2001 |
| WO | 2001076510 A2 | 10/2001 |
| WO | 2002036048 A1 | 5/2002 |
| WO | 0247575 A2 | 6/2002 |
| WO | 02067782 A2 | 9/2002 |
| WO | 2003047468 A1 | 6/2003 |
| WO | 2005062980 A2 | 7/2005 |
| WO | 2005070343 A1 | 8/2005 |
| WO | 2006073626 A2 | 7/2006 |
| WO | 2007071436 A2 | 6/2007 |
| WO | 2008070797 A2 | 6/2008 |
| WO | 2009024859 A2 | 2/2009 |
| WO | 2009042196 A2 | 4/2009 |
| WO | 2010008548 A2 | 1/2010 |
| WO | 2010008548 A2 | 1/2010 |
| WO | 2010096176 A1 | 8/2010 |
| WO | 2010098857 A1 | 9/2010 |
| WO | 2011133787 A1 | 10/2011 |
| WO | 2012048035 A2 | 4/2012 |
| WO | 2012177942 A2 | 12/2012 |
| WO | 2013028387 A2 | 2/2013 |
| WO | 2014163704 A1 | 10/2014 |
| WO | 2014164149 A1 | 10/2014 |
| WO | 2014164151 A1 | 10/2014 |
| WO | 2015077274 A1 | 5/2015 |

OTHER PUBLICATIONS

Andersen HR, Knudsen LL, Hasenkam JM. Transluminal implantation of artificial heart valves. Description of a new expandable aortic valve and initial results with implantation by catheter technique in closed chest pigs. European heart Journal. May 1, 1992;13(5):704-8.

Andersen, Henning Rud, Transluminal Catheter Implanted Prosthetic Heart Valves, International Journal of Angiology 7:102-106 (1998).

Braido, et al., U.S. Appl. No. 29/375,243, filed Sep. 20, 2010, titled "Surgical Stent Assembly".

Braido, Peter N., U.S. Appl. No. 61/931,265, filed Jan. 24, 2014; Stationary Intra-Annular Halo Designs for Paravalvular Leak (PVL) Reduction—Active Channel Filling Cuff Designs.

Buellesfeld, et al., "Treatment of paravalvular leaks through inverventional techniques," Multimed Man Cardiothorac Surg., Department of Cardiology, Ben University Hospital, pp. 1-8, Jan. 2011.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Dewey, et al., "Transapical Aortic Valve Implantation: An Animal Feasibility Study", The Annals of Thoracic Surgery, vol. 82, No. 1, Jul. 2006, pp. 110-116.

Gössl et al., "Percutaneous Treatment of Aortic and Mitral Valve Paravalvular Regurgitation", Current Cardiology Reports, vol. 15, No. 8, Aug. 2013, pp. 1-8.

Heat Advisor, "Heart Repairs Without Surgery: Minimally Invasive Procedures Aim to Correct Valve Leakage", Technology Frontier, Sep. 2004, pp. 4-5.

Hijazi et al., Transcatheter Valve Repair, CRC Press, Jan. 2006, pp. 165-186.

Hourihan, et al., "Transcatheter Umbrella Closure of Valvular and Paravalvular Leaks," Journal of the American College of Cardiology, vol. 20, No. 6, pp. 1371-1377, Nov. 1992.

Huber, et al., "Direct-Access Valve Replacement: A Novel Approach for Off-Pump Valve Implantation Using Valved Stents", Journal of the American College of Cardiology, vol. 46, No. 2, Jul. 2005, pp. 366-370.

International Search Report and Written Opinion for Application No. PCT/US2015/011387 dated Mar. 30, 2015, 26 pages.

Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993;16(5):253-62.

Mack, "Minimally invasive cardiac surgery", Surgical Endoscopy, 2006, 20:S488-S492, DOI: 10.1007/s00464-006-0110-8, presented Apr. 24, 2006.

Moazami et al., "Transluminal Aortic Valve Placement: A Feasibility Study With a Newly designed Collapsible Aortic Valve.", ASAIO Journal, (Sep. 1996), vol. 42, pp. M381-M385, XP000683605.

Preliminary Opinion of the Opposition Division Indicating Issue of Summons to Follow at a Later Time and Shorter Notice for EP15152324.8 dated May 13, 2020; 12 pages.

Rodriguez et al., "Guidance of Treatment of Pehvalvular Prosthetic Leaks", Current Cardiology Reports, vol. 16, No. 1, Nov. 2013, pp. 1-6.

Rohde, et al., "Resection of Calcified Aortic Heart Leaflets In Vitro by Q-Switched 2 pm Microsecond Laser Radiation", Journal of Cardiac Surgery, 30(2): 157-62. Feb. 2015.

Samuel V. Lichtenstein et al., Transapical Transcatheter Aortic Valve Implantation in Humans, Circulation, Jul. 2006, pp. 591-596, vol. 114.

Samuel V. Lichtenstein, "Closed heart surgery: Back to the future", The Journal of Thoracic and Cardiovascular Surgery, vol. 131, No. 5, pp. 941-943, May 2006.

Swiatkiewicz, et al., "Percutaneous closure of mitral perivalvular leak," Kardiologia Polska, vol. 67, No. 7, pp. 762-764, Jul. 2009.

Walther et al., "Transapical approach for sutureless stent-fixed aortic valve implantation: experimental results", European Journal of Cardio-thoracic Surgery, vol. 29(5), pp. 703-708 (Jan. 30, 2006).

Webb et al., "Percutaneous Aortic Valve Implantation Retrograde From the Femoral Artery", Circulation, published online Feb. 2006, pp. 842-850, vol. 113, American Heart Association, Dallas, TX, USA.

Zegdi, Rachid, MD, PhD et al., "Is It Reasonable to Treat All Calcified Stenotic Aortic Valves With a Valved Stent?" 579-584, J. of the American College of Cardiology, vol. 51. No. 5, Feb. 5, 2008.

* cited by examiner

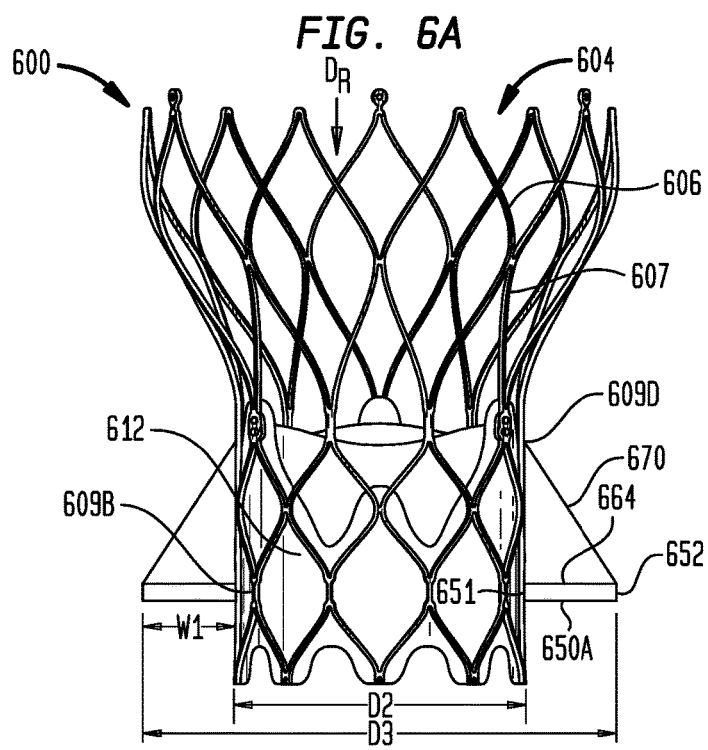
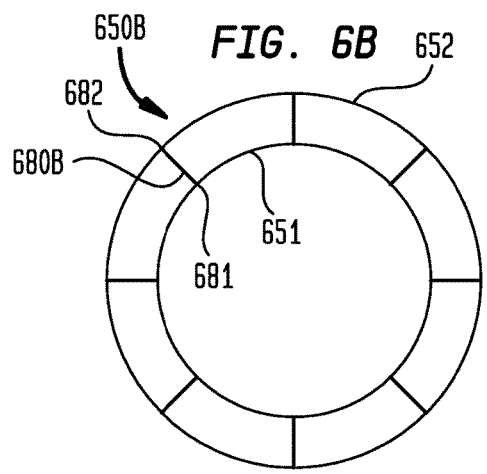
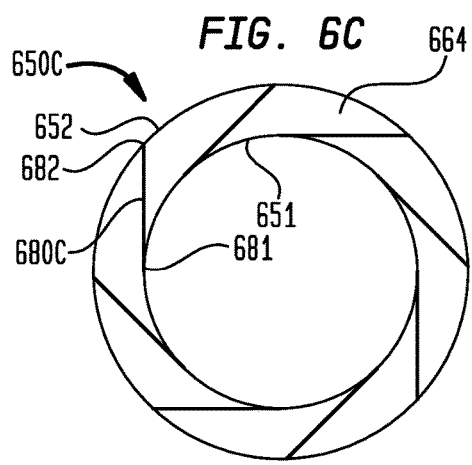
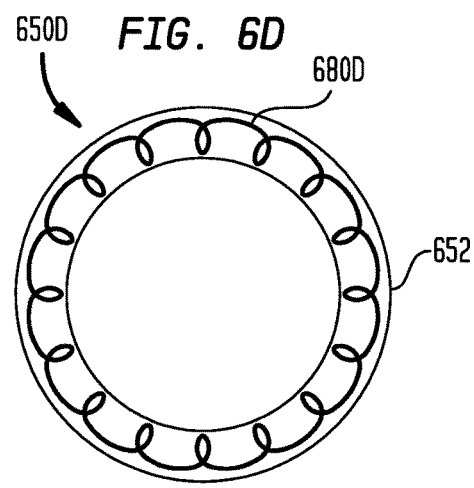
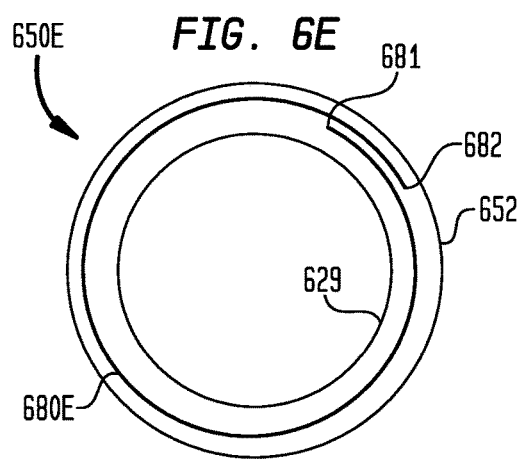
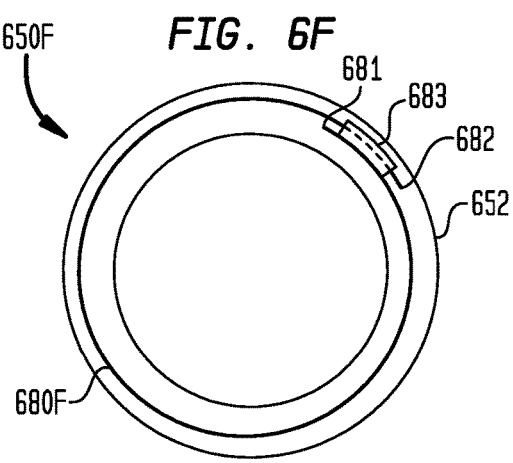

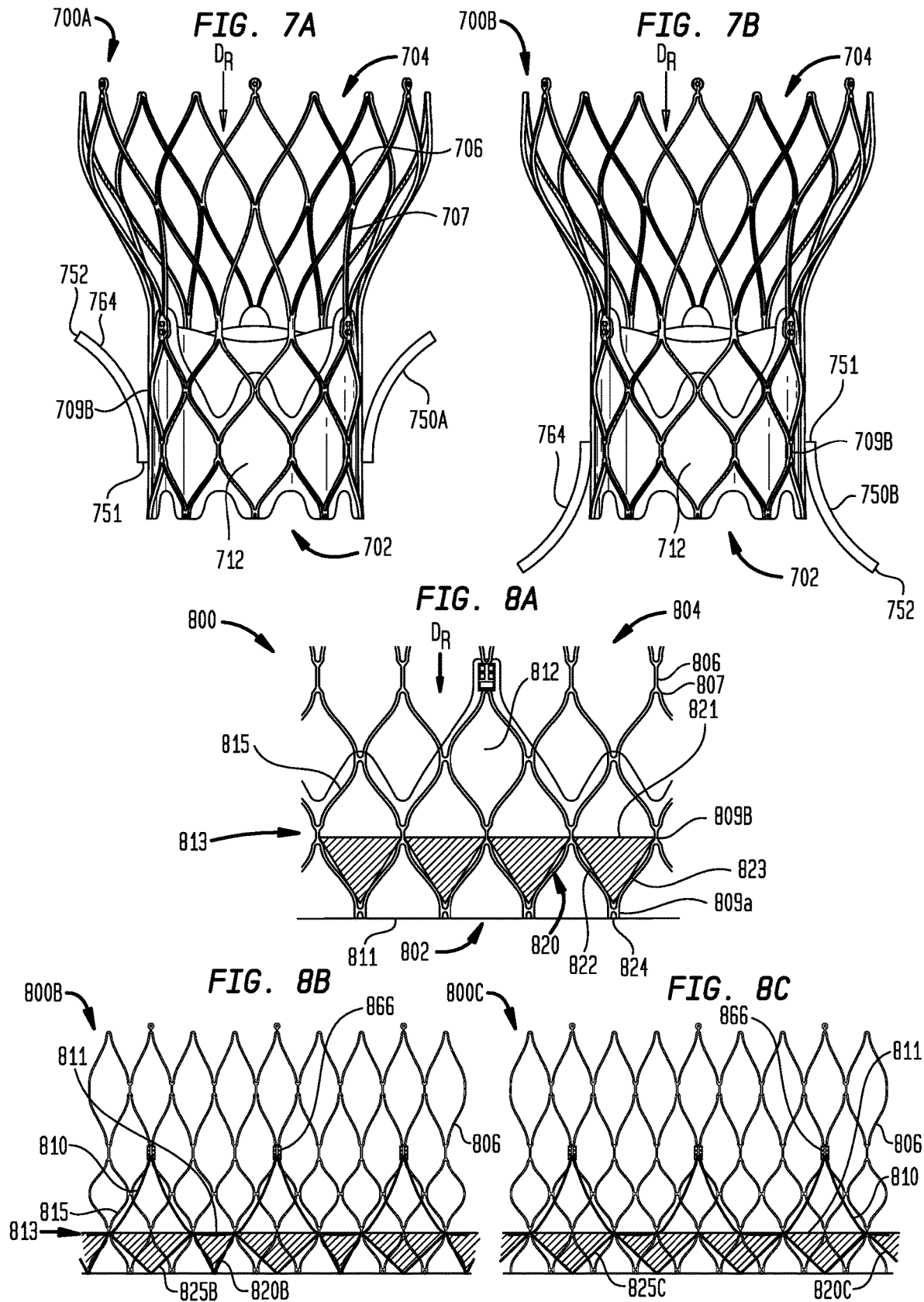

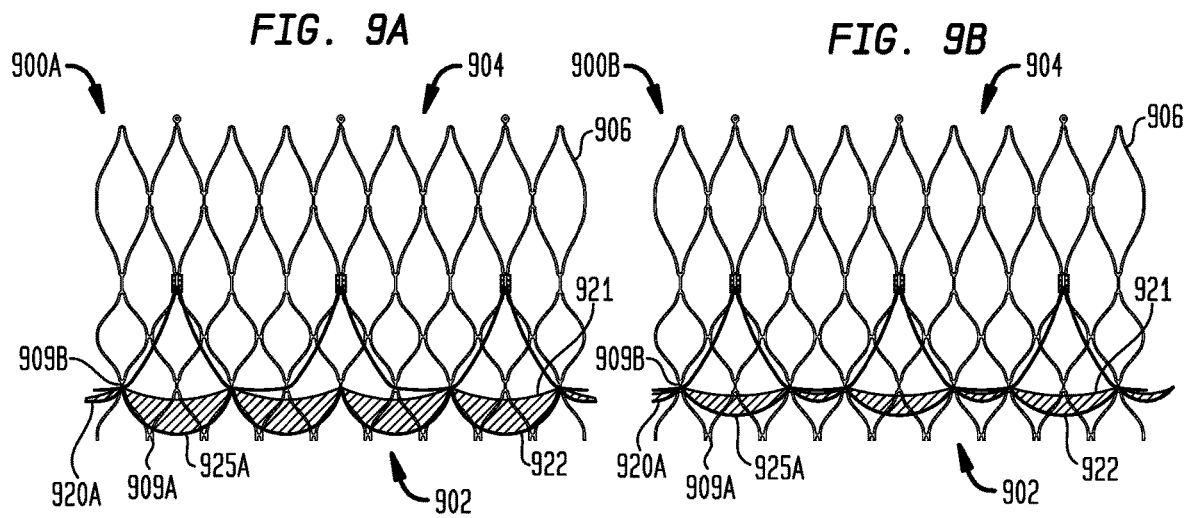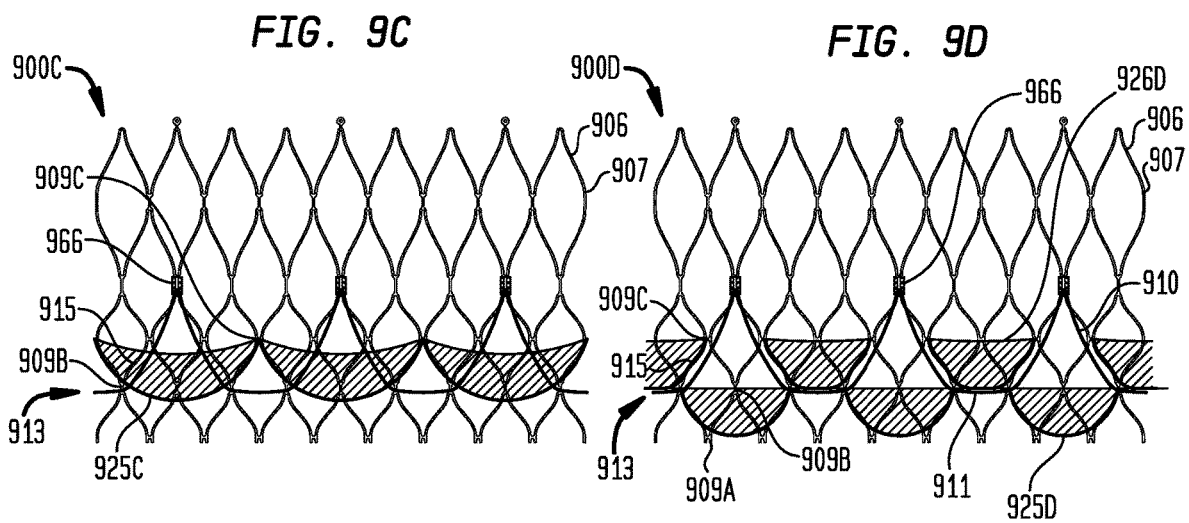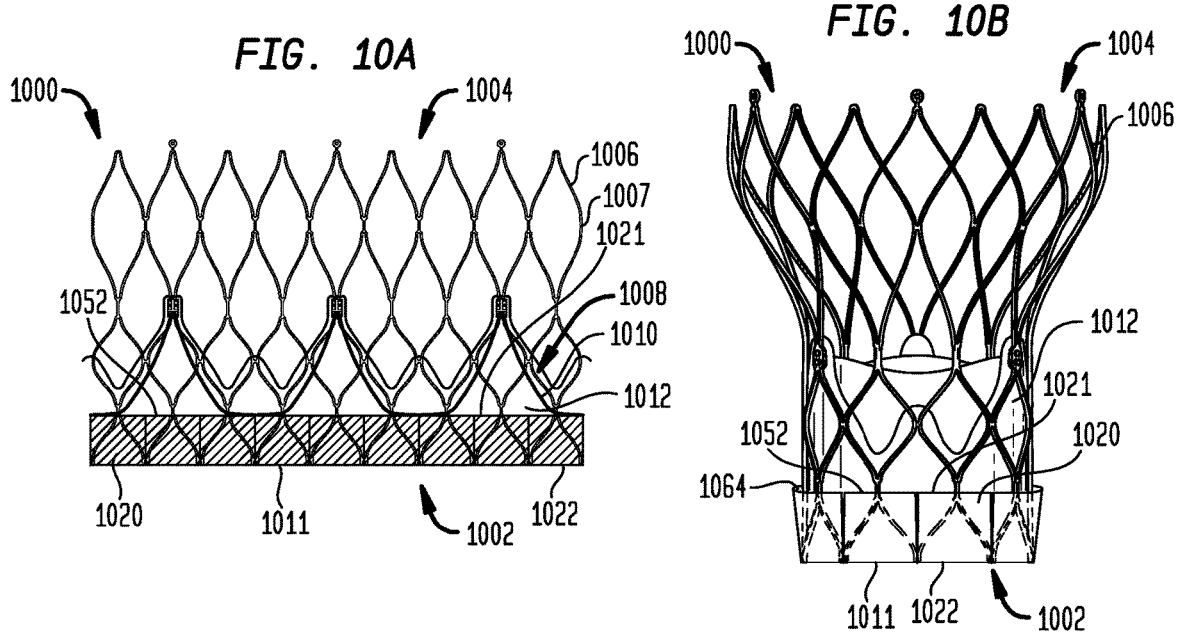

STATIONARY INTRA-ANNULAR HALO DESIGNS FOR PARAVALVULAR LEAK (PVL) REDUCTION—ACTIVE CHANNEL FILLING CUFF DESIGNS

CROSS-REFERENCE TO RELATED APPLICATIONS

The present application is a continuation of U.S. patent application Ser. No. 16/680,782 filed Nov. 12, 2019, now U.S. Pat. No. 11,419,716, which is a continuation of U.S. patent application Ser. No. 15/710,007 filed Sep. 20, 2017, now U.S. Pat. No. 10,500,039, which is a divisional application of U.S. patent application Ser. No. 14/601,810 filed Jan. 21, 2015, now U.S. Pat. No. 9,820,852, which claims the benefit of the filing date of U.S. Provisional Patent Application No. 61/931,265 filed Jan. 24, 2014, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

BRIEF SUMMARY OF THE INVENTION

Prosthetic heart valves and methods of expanding a prosthetic heart valve between native leaflets of a native aortic annulus of a patient are disclosed.

A prosthetic heart valve configured to be expanded between leaflets of a native aortic valve of a patient may include a collapsible and expandable stent extending in a flow direction between a proximal end and a distal end, a cuff attached to an annulus section of the stent and having an outer surface facing in a radial direction orthogonal to the flow direction, a plurality of prosthetic valve leaflets attached to the cuff, and a sealing structure attached to the annulus section of the stent at an inner edge of the sealing structure.

The annulus section of the stent may be adjacent the proximal end, and the stent may include a plurality of struts shaped to form a plurality of cells connected to one another in a plurality of annular rows around the stent. The flow direction may be defined from the proximal end toward the distal end. The sealing structure may have an outer edge remote from the inner edge. The sealing structure may have a collapsed condition with the outer edge disposed adjacent the outer surface of the cuff and an expanded condition with the outer edge spaced apart from the outer surface of the cuff.

In the expanded condition of the sealing structure, a top surface of the cuff extending between the inner and outer edges thereof may generally face toward the distal end of the stent in the flow direction. The top surface may include a plurality of openings in fluid communication with an interior of the sealing structure. The top surface of the sealing structure may include a porous material having a multitude of small apertures adapted to allow unidirectional blood flow into an interior of the sealing structure. The sealing structure may extend continuously around a circumference of the stent.

In the expanded condition of the sealing structure, an inner end portion of the top surface may be disposed adjacent the outer surface of the cuff and an outer end portion of the top surface may extend away from the outer surface of the cuff at a transverse angle to the flow direction. The prosthetic heart valve may also include a plurality of support members each extending between the stent and the outer edge of the sealing structure. The prosthetic heart valve may also include at least one stored energy element biased to provide a force to the sealing structure away from the cuff in a radial direction orthogonal to the flow direction when at least a portion of the sealing structure is radially compressed toward the cuff.

The at least one stored energy element may include a plurality of storage elements circumferentially spaced apart from one another between the inner edge and the outer edge of the sealing structure. The at least one stored energy element may include a spring that extends in at least one complete loop about a circumference of the sealing structure between the inner edge and the outer edge.

A prosthetic heart valve configured to be expanded between leaflets of a native aortic valve of a patient may include a collapsible and expandable stent extending in a flow direction between a proximal end and a distal end, a cuff attached to an annulus section of the stent and having an outer surface facing in a radial direction orthogonal to the flow direction, a plurality of prosthetic valve leaflets attached to the cuff, and a plurality of sealing members each attached to the annulus section of the cuff.

The annulus section of the stent may be adjacent the proximal end, and the stent may include a plurality of struts shaped to form a plurality of cells connected to one another in a plurality of annular rows around the stent. The flow direction may be the direction from the proximal end toward the distal end. Each sealing member may have an open side facing generally toward the distal end of the stent and a closed side facing generally toward the proximal end of the stent, so that blood flowing in a direction opposite the flow direction will enter at least one of the sealing members through the open side and cause an outer surface of the at least one sealing member to move away from the outer surface of the cuff.

Each sealing member may have a shape selected from the group consisting of generally triangular, generally crescent-shaped, generally rectangular, or generally square. The plurality of sealing members may collectively extend completely around a circumference of the stent. Each of the sealing members may be entirely located between the proximal end of the stent and locations at which the leaflets are attached to the cuff. The stent may include commissure features each located at a juncture of adjacent ones of the leaflets. At least a portion of each leaflet may be attached to one of the commissure features. Each of the sealing members may be substantially aligned in the flow direction with a corresponding one of the commissure features.

The plurality of sealing members may include a first group of sealing members having a first width and a second group of sealing members having a second width less than the first width. Each of the sealing members in the first group may extend around a greater portion of a circumference of the stent than each of the sealing members in the second group. The stent may include commissure features each located at a juncture of adjacent ones of the leaflets. At least a portion of each leaflet may be attached to one of the commissure features. The sealing members in the first group may be substantially aligned in the flow direction with the commissure features.

Each of the sealing members in the second group may be substantially aligned in the flow direction with portions of the leaflets that are attached to the cuff closest to the proximal end of the stent. The sealing members may include lower sealing members and upper sealing members. The upper sealing members may be spaced in the flow direction of the stent above the lower sealing members.

The plurality of sealing members may include a group of lower sealing members and a group of upper sealing members. The open sides of the sealing members in the lower group may be spaced a first distance from the proximal end of the stent in the flow direction. Open sides of the sealing members in the upper group may be spaced a second distance from the proximal end of the stent in the flow direction. The second distance may be greater than the first distance.

The open sides of the lower sealing members may be spaced apart about a circumference of the stent by first openings. The open sides of the upper sealing members may be spaced apart about the circumference of the stent by second openings. The open sides of the upper sealing members may be aligned in the flow direction with the first openings, and the open sides of the lower sealing members may be aligned in the flow direction with the second openings, such that any blood flow in a direction opposite the flow direction along the outer surface of the cuff will encounter at least one of the open sides of the upper or lower sealing members.

BRIEF DESCRIPTION OF THE DRAWINGS

Various embodiments of heart valves are disclosed herein with reference to the drawings, wherein:

FIG. 6A is a schematic side view of another embodiment of a heart valve having a sealing ring intended to fill irregularities between the heart valve and the native valve annulus;

FIGS. 6B-6F are highly schematic top views of alternative sealing ring embodiments that can be used with the stent, cuff, and leaflets of FIG. 6A;

FIGS. 7A and 7B are schematic side views of alternative embodiments of heart valves having a sealing ring intended to fill irregularities between the heart valve and the native valve annulus;

FIG. 8A is a partial developed view of the stent, sealing members, and cuff of another embodiment of a heart valve having sealing members intended to fill irregularities between the heart valve and the native valve annulus;

FIGS. 8B and 8C are developed views of the stent and cuff of FIG. 8A, with alternative sealing members;

FIG. 9A is a developed view of the stent, sealing members, and leaflets of another embodiment of a heart valve having sealing members intended to fill irregularities between the heart valve and the native valve annulus;

FIGS. 9B-9D are developed views the stent and leaflets of FIG. 9A, with alternative sealing members;

FIG. 10A is a developed view of the stent, sealing members, and leaflets of another embodiment of a heart valve having sealing members intended to fill irregularities between the heart valve and the native valve annulus; and FIG. 10B is a side view of a heart valve having the stent and sealing members of FIG. 10A.

Figure 1:
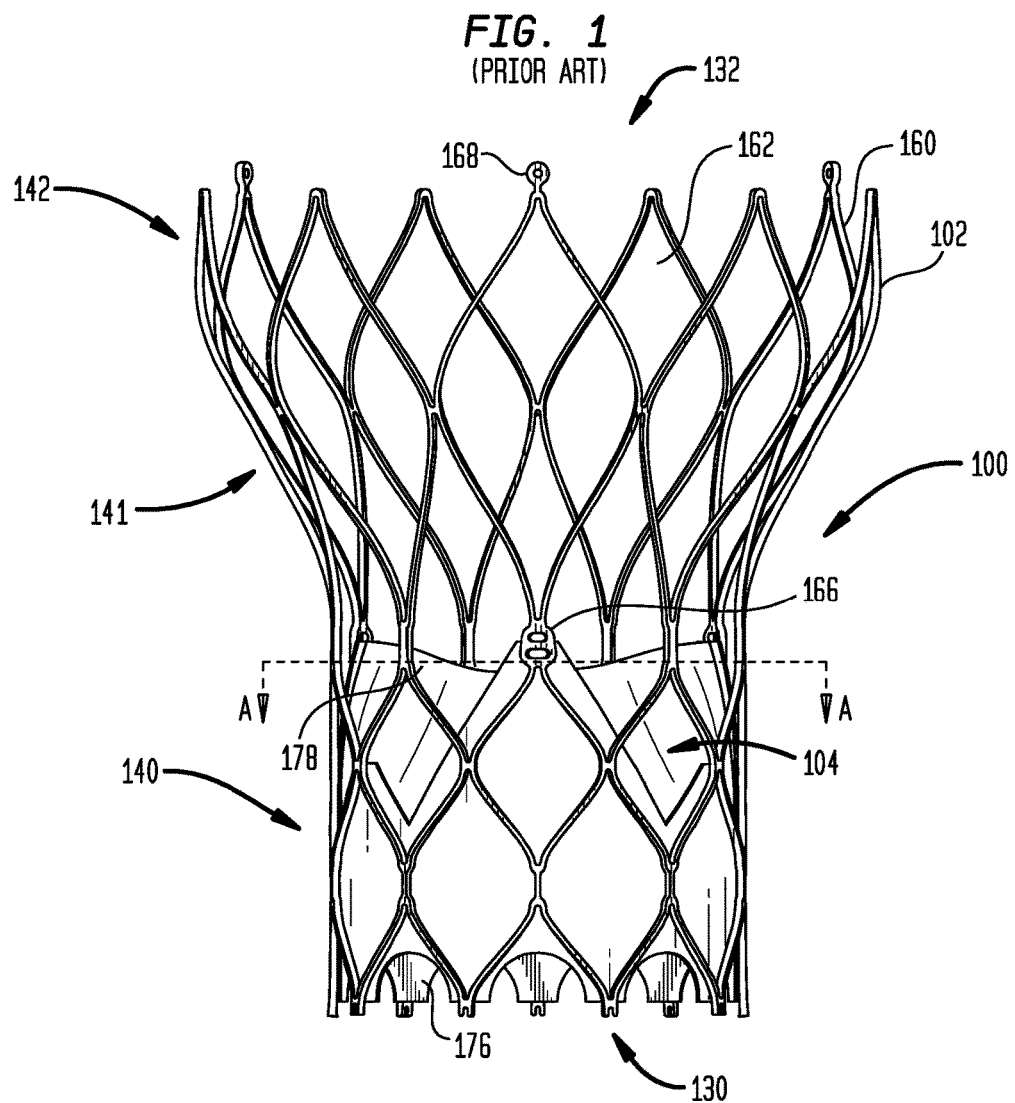
FIG. 1 is a side elevational view of a conventional prosthetic heart valve.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

With conventional self expanding valves, clinical success of the valve is dependent on accurate deployment and anchoring. One possibility on valve implantation is leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the procedure as well as the risk of post-operative problems. Thus, methods and devices are desirable that would reduce the need to remove a prosthetic heart valve from a patient. Methods and devices are also desirable that would reduce the likelihood of perivalvular leakage due to gaps between the implanted heart valve and patient tissue.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user. Also as used herein, the terms "generally," "substantially," "approximately," and "about" are intended to mean that slight deviations from absolute are included within the scope of the term so modified.

When used to indicate relative locations within the aortic annulus, the aortic root, and the ascending aorta of a patient, the terms "above" and "below" are to be taken as relative to the juncture between the aortic annulus and the left ventricle. "Above" is to be understood as relatively farther from the left ventricle, and "below" is to be understood as relatively closer to the left ventricle.

When used to indicate relative locations within the prosthetic heart valve, the terms "longitudinal" and "vertical" are to be taken as the direction of the axis extending between the proximal end and the distal end of the stent of the heart valve, along the direction of intended blood flow; the term "flow direction" is to be taken as the direction from the proximal end to the distal end of the stent of the heart valve, along the direction of intended blood flow; and the terms "above," "below," "high," and "low" are to be taken as relative to the proximal end of the stent. "Above" and "high" are to be understood as relatively farther from the proximal end of the stent in the flow direction toward the distal end of the stent, and "below" and "low" are to be understood as relatively closer to the proximal end of the stent in the flow direction. When used to indicate relative locations within the prosthetic heart valve, the term "circumferential" is to be taken as the direction of rotation about an axis extending in the flow direction of the stent.

The sealing portions of the present disclosure may be used in connection with collapsible prosthetic heart valves. FIG. 1 shows one such collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the inventions herein are described predominantly in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

The stent 102 may be formed from biocompatible materials that are capable of self-expansion, such as, for example, shape memory alloys, such as the nickel-titanium alloy known as "Nitinol" or other suitable metals or polymers. The stent 102 extends from a proximal or annulus end 130 to a distal or aortic end 132, and includes an annulus section 140 adjacent the proximal end 130, a transition section 141, and an aortic section 142 adjacent the distal end 132. The annulus section 140 has a relatively small cross-section in the expanded condition, while the aortic section 142 has a relatively large cross-section in the expanded condition. The annulus section 140 may be in the form of a cylinder having a substantially constant diameter along its length. The transition section 141 may taper outwardly from the annulus section 140 to the aortic section 142.

Each of the sections of the stent 102 includes a plurality of struts 160 forming cells 162 connected to one another in one or more annular rows around the stent. For example, as shown in FIG. 1, the annulus section 140 may have two annular rows of complete cells 162 and the aortic section 142 and the transition section 141 may each have one or more annular rows of partial cells 162. The cells 162 in the aortic section 142 may be larger than the cells 162 in the annulus section 140. The larger cells in the aortic section 142 better enable the prosthetic valve 100 to be positioned in the native valve annulus without the stent structure interfering with blood flow to the coronary arteries.

The stent 102 may include one or more retaining elements 168 at the distal end 132 thereof, the retaining elements 168 being sized and shaped to cooperate with female retaining structures (not shown) provided on the deployment device. The engagement of the retaining elements 168 with the female retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

The prosthetic heart valve 100 includes a valve assembly 104 preferably positioned in the annulus section 140 of the stent 102 and secured to the stent. The valve assembly 104 includes a cuff 176 and a plurality of leaflets 178 which collectively function as a one-way valve by coapting with one another. As a prosthetic aortic valve, the prosthetic heart valve 100 has three leaflets 178. However, it will be appreciated that other prosthetic heart valves with which the sealing portions of the present disclosure may be used may have a greater or lesser number of leaflets 178.

Although the cuff 176 is shown in FIG. 1 as being disposed on the luminal or inner surface of the annulus section 140, it is contemplated that the cuff 176 may be disposed on the abluminal or outer surface of the annulus section 140 or may cover all or part of either or both of the luminal and abluminal surfaces. Both the cuff 176 and the leaflets 178 may be wholly or partly formed of any suitable biological material or polymer such as, for example, polytetrafluoroethylene (PTFE), polyvinyl alcohol (PVA), ultra-high molecular weight polyethylene (UHMWPE), silicone, urethane and the like.

The leaflets 178 may be attached along their belly portions to the cells 162 of the stent 102, with the commissure between adjacent leaflets 178 being attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, the commissure features 166 are positioned entirely within the annulus section 140 or at the juncture of the annulus section 140 and the transition section 141. The commissure features 166 may include one or more eyelets which facilitate the suturing of the leaflet commissure to the stent 102.

The prosthetic heart valve 100 may be used to replace a native aortic valve, a surgical heart valve, or a heart valve that has undergone a surgical procedure. The prosthetic heart valve 100 may be delivered to the desired site (e.g., near the native aortic annulus) using any suitable delivery device. During delivery, the prosthetic heart valve 100 is disposed inside the delivery device in the collapsed condition. The delivery device may be introduced into a patient using a transfemoral, transapical, transseptal, transradial, transsubclavian, transaortic or any other percutaneous approach. Once the delivery device has reached the target site, the user may deploy the prosthetic heart valve 100. Upon deployment, the prosthetic heart valve 100 expands so that the annulus section 140 is in secure engagement within the native aortic annulus. When the prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting the prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly-calcified leaflets for proper valve placement and seating could lead to several problems, such as perivalvular leakage ("PV leak"), which can have severe adverse clinical outcomes. To reduce these adverse events, the optimal valve would anchor adequately and seal without the need for excessive radial force that could harm nearby anatomy and physiology.

PV leak may also be caused by the implantation of a valve having an expanded diameter that is too small relative to the native aortic annulus diameter, a prosthetic valve that is deployed in a tilted orientation relative to the native aortic annulus (such that the longitudinal axis of the valve and the native aortic annulus are misaligned), lack of full radial expansion of the valve due to the stent catching on calcific nodules in the native aortic annulus, and placing the valve at a non-optimal longitudinal position relative to the native aortic annulus (either too high or too low along a longitudinal axis of the native aortic annulus).

Figures 2A, 2B:
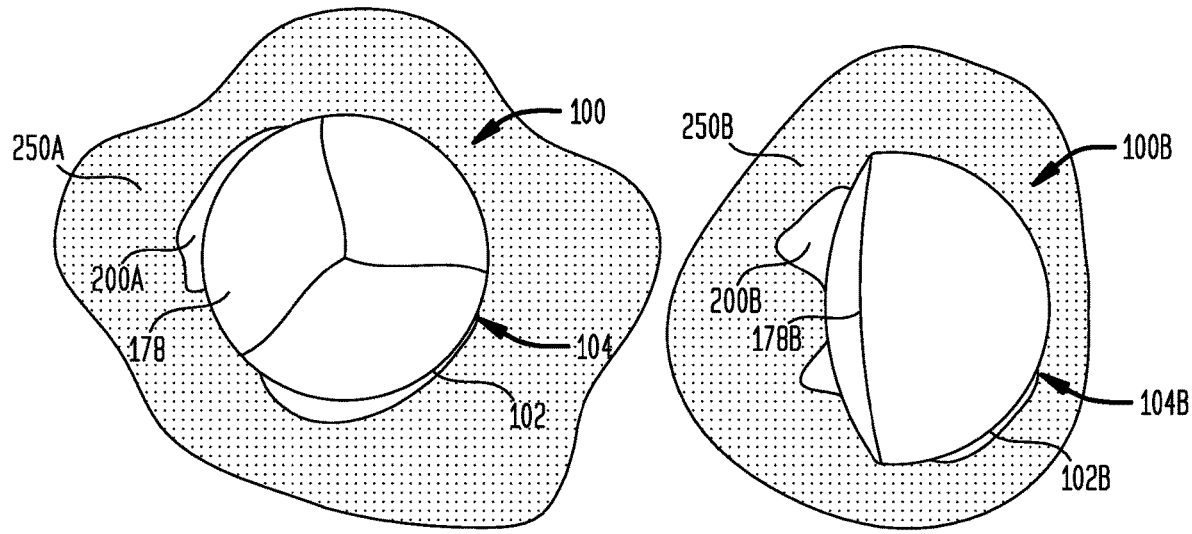
FIG. 2A is a highly schematic cross-sectional view taken along line A-A of FIG. 1 and showing the prosthetic heart valve disposed within a native valve annulus.
FIG. 2B is a highly schematic cross-sectional view showing a prosthetic mitral valve disposed within a native valve annulus.

FIG. 2A is a highly schematic cross-sectional illustration of the prosthetic heart valve 100 disposed within a native valve annulus 250A. As seen in the figure, the prosthetic heart valve 100 has a substantially circular cross-section which is disposed within the non-circular native valve annulus 250A. At certain locations around the perimeter of the heart valve 100, gaps 200A form between the heart valve 100 and the native valve annulus 250A. Blood flowing through these gaps and past the valve assembly 104 of the prosthetic heart valve 100 can cause regurgitation and other inefficiencies which reduce cardiac performance. Such improper fitment may be due to suboptimal native valve annulus geometry due, for example, to calcification of the native valve annulus 250A or to unresected native leaflets.

FIG. 2B is a similar cross-sectional illustration of a prosthetic mitral valve 100B disposed within a native valve annulus 250B. As seen in the figure, the prosthetic mitral valve 100B has a substantially D-shaped cross-section that is disposed within the irregularly-shaped annulus 250B. At certain locations around the perimeter of the heart valve 100B, gaps 200B form between the heart valve 100B and the native valve annulus 250B. Regurgitation and other inefficiencies may thus result after deployment of a prosthetic mitral valve. Though the following examples show aortic valves, it will be understood that the present devices and methods may be equally applicable to mitral heart valves, as well as to pulmonary valves and tricuspid valves.

Figure 3A:
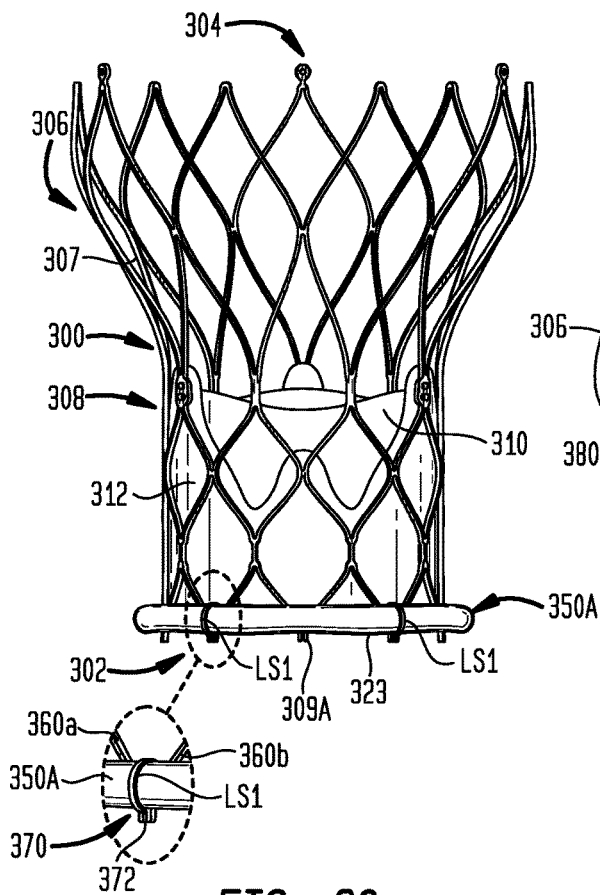
FIG. 3A is a highly schematic side view of another embodiment of a heart valve having a sealing ring intended to fill irregularities between the heart valve and the native valve annulus.
Figure 3B:
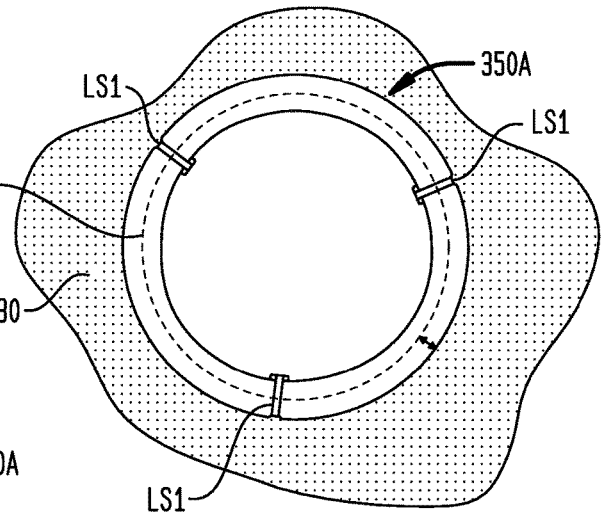
FIG. 3B is a schematic end view of the prosthetic heart valve of FIG. 3A as seen from the annulus end toward the aortic end of the heart valve.

FIGS. 3A and 3B illustrate a prosthetic heart valve 300 in accordance with another embodiment. As can be seen in FIG. 3A, the prosthetic heart valve 300 extends between a proximal end 302 and a distal end 304, and may generally include a stent 306 formed of a plurality of struts 307, and a valve assembly 308 having a plurality of leaflets 310 and a cuff 312.

The prosthetic heart valve 300 further includes a generally toroidal-shaped sealing ring 350A that may be annularly disposed around the abluminal surface of the stent 306 at the proximal end 302 of the prosthetic heart valve 300 (e.g., at a position that will lie at least partially below the native valve annulus when the prosthetic heart valve is deployed into a patient). The sealing ring 350A may be formed, for example, from a long, thin rectangle of material about 10 mm in width that is folded approximately in half longitudinally, and the opposed longitudinal edges may be stitched to one another to create a flattened tube about 5 mm in diameter. The lateral ends of the flattened tube may be stitched to one another to create the sealing ring 350A.

Although the sealing ring 350A is shown in FIG. 3A as having a circular cross-section, that need not be the case. The sealing ring 350A may be flattened in the flow direction, or it may have a cross-section that is square, rectangular, triangular, or other shapes. It is to be understood that all of the "sealing rings" described herein are not to be understood to be limited to having a circular cross-section. Any of the sealing rings described herein may be flattened in the flow direction, or they may have a cross-section that is square, rectangular, triangular, or other shapes.

A proximal surface 323 of the sealing ring is substantially aligned in the flow direction of the stent with the proximalmost junctions 309A (FIG. 3A) of the stent. The sealing ring 350A may have a radius larger than that of the valve assembly 308, the larger radius of the sealing ring being capable of filling and/or blocking blood flow through gaps between the prosthetic heart valve 300 and the native valve annulus (not shown).

The longitudinal seam of the sealing ring 350A may be stitched to an abluminal surface of the cuff 312 and to select struts 307 of the stent 306 by sutures that secure the sealing ring in place. In some examples, the sutures may be the same sutures as are used to attach the cuff 312 to the struts 307 so that no extra steps or bulk is added.

In one example, as seen in the enlarged schematic view of FIG. 3A, end struts 360a and 360b of the stent 306 meet to form a horseshoe-shaped end 370 having a partial slot 372 therebetween. A number of locking stitches LS1 may be tied around the horseshoe-shaped ends 370, and specifically through each slot 372 and around the sealing ring 350A to secure it to the stent 306. The locking stitches LS1 may be formed of a suture, string, or any other suitable biocompatible thread.

It will be understood that, though three locking stitches are shown around the circumference of the prosthetic heart valve to couple the sealing ring 350A to the stent 306, any number of locking stitches may be used. Although the locking stitches LS1 are shown in FIGS. 3A and 3B as extending completely around the sealing ring 350A, that need not be the case. In other examples, the sealing ring 350A may be attached to the stent 306 by sutures stitched through a portion of an inner diameter of the sealing ring. Other techniques for maintaining the shape of the sealing ring 350A may also be used including adhesive, glue, shape memory fabric, or the like.

The sealing ring 350A may be formed of the same material as the cuff 312, or of a different material that is sutured, glued or otherwise affixed to the proximal end of the cuff. In one example, the sealing ring 350A may be made of a thin tubular fabric material. In other examples, the sealing ring 350A may include thin porcine pericardial tissue between about 0.005 inches and about 0.007 inches in thickness, or UHMWPE or PET fabric between about 0.003 inches and about 0.005 inches in thickness.

Alternatively, a variety of other materials may be used, including bovine tissue (e.g., glycerol impregnated or freeze dried), tissue with support structures therein, wire mesh, radiopaque wire, fabric, braided or woven fabric (e.g., PTFE, PTE, or UHMWPE), fabric coated with PTFE or collagen, or a multi-layered composite of one or more of the aforementioned materials (e.g., a fabric and tissue composite). Any of the sealing rings or sealing members disclosed herein may be made of any one of the aforementioned materials or a combination thereof.

The sealing ring 350A may be at least partially radiopaque, i.e., the sealing ring may include one or more materials having enhanced visibility to a user under fluoroscopy. For example, the sealing ring 450C may be include fabric or wire mesh material having radiopaque fibers or entirely comprised of radiopaque fibers. The sealing ring 450C may include radiopaque marker beads, a thin radiopaque wire, radiopaque paint, or impregnation by soaking in a radiopaque material such as silver, iodine, barium, platinum, or the like. Any of the sealing rings or sealing members disclosed herein may be made of any one of the aforementioned radiopaque materials or a combination thereof.

FIG. 3B illustrates the prosthetic heart valve 300 in native valve annulus 380 after formation of the sealing ring 350A as seen from the proximal end 302 (e.g., as seen from the annulus end toward the aortic end of the heart valve). The sealing ring 350A has been secured to the stent 306 via a series of locking stitches LS1. The outer diameter of the stent 306 at the proximal end is indicated with a dashed line. The sealing ring 350A extends radially outward from the outer diameter of the stent 306 at the proximal end of the prosthetic heart valve 300 by a radial distance r1. In at least some examples, the radial distance r1 may be between about 1.0 mm and about 2.5 mm. The radial distance r1 may preferably be between at least 2.0 mm.

As can be seen in FIGS. 3A and 3B, the sealing ring 350A is configured to radially expand to a diameter greater than the diameter of the proximal end 302 of the stent 306 when the stent is radially expanded, extending radially outward from the outer diameter of the stent by the radial distance r1, for example. To ensure that the sealing ring 350A radially expands to a diameter greater than the diameter of the proximal end 302 of the stent 306 when the prosthetic heart valve 300 is deployed into a patient, the sealing ring 350A, and all of the other sealing rings described herein, may have sufficient elasticity that it has a spring bias that tends to provide a force in a radially outward direction when the sealing ring is radially compressed.

However, the outward spring bias of the sealing ring 350A, and of all of the other sealing rings described herein, is preferably small enough that the sealing ring may expand a greater radial distance at locations along the circumference of the sealing ring at which there is minimal radial force applied to the sealing ring from the native anatomy (i.e., at locations at which voids or gaps between the stent 306 and the native anatomy are present), while the sealing ring may expand a lesser radial distance at locations along the circumference of the sealing ring at which there is greater radial force applied to the sealing ring from the native anatomy (i.e., locations at which there are no such voids or gaps).

Figure 3C:
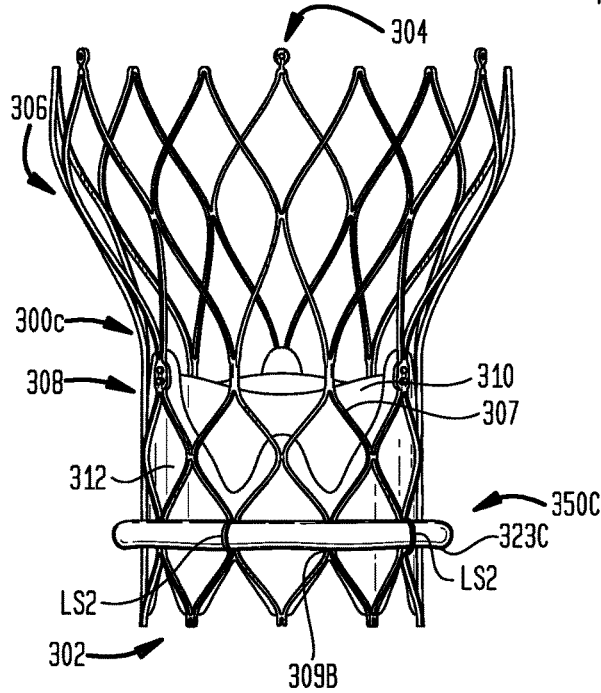
FIG. 3C is a highly schematic side view of a variation of the embodiment shown in FIGS. 3A and 3B.

FIG. 3C illustrates a heart valve 300C, which is a variant of the heart valve 300 of FIGS. 3A and 3B. The heart valve 300C has a sealing ring 350C disposed at a higher location along the stent 306 than the sealing ring 350A of FIG. 3A, which may permit the prosthetic heart valve 300C to achieve improved sealing against the native annulus and the native leaflets in some patients.

Compared to the sealing ring 350A of FIGS. 3A and 3B, all of the other sealing rings described herein, including the sealing ring 350C, have structures that may provide different surface areas and thicknesses of material at different longitudinal and circumferential locations relative to the stent to provide different advantages in sealing voids or gaps between the stent and the native anatomy when the heart valves are deployed into a patient. Such differences in surface areas and thicknesses of material at certain longitudinal and circumferential locations may make some sealing ring configurations preferable for certain native anatomies and other sealing ring configurations preferable for other native anatomies, depending on the anticipated locations of voids or gaps between a deployed prosthetic heart valve and the native anatomy. Such anticipated locations of voids or gaps between a deployed prosthetic heart valve and the native anatomy may be determined by a variety of methods, including imaging of the native anatomy before deployment of a prosthetic heart valve, for example.

The heart valve 300C extends between a proximal end 302 and a distal end 304, and may generally include a stent 306 formed of struts 307, and a valve assembly 308 having a plurality of leaflets 310 and a cuff 312. The sealing ring 350C has been positioned so that the proximal surface 323C of the sealing ring lies above the proximal end 302 of the stent 306 and closer to the leaflets 310 than the sealing ring 350A (e.g., at a position that will lie within the native valve annulus when the prosthetic heart valve is deployed into a patient). After positioning the sealing ring 350C at the appropriate position, locking stitches LS2 may be coupled to the sealing ring 350C and to upper junctions 309B of the proximalmost struts 307 of the stent 306 to secure the sealing ring in place.

Figure 4:
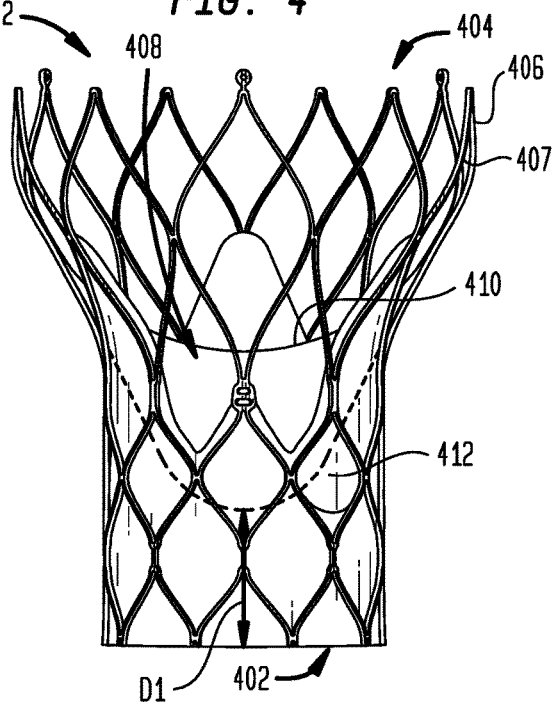
FIG. 4 is a side view of another embodiment of a heart valve having a higher cuff height.

FIG. 4 illustrates a prosthetic heart valve 400, which is a variant of the prosthetic heart valve 100 of FIG. 1. The heart valve 400 extends between a proximal end 402 and a distal end 404, and may generally include a stent 406 formed of struts 407, and a valve assembly 408 having a plurality of leaflets 410 and a cuff 412.

As shown in FIG. 4, in the prosthetic heart valve 400, the cuff 412 may extend over a greater distance in a flow direction of the stent 406 compared to the cuff 112 of FIG. 1. For example, when the stent 406 is in an expanded use condition, a landing zone (i.e., continuous cylindrical portion) of the cuff 412 may extend over a length of about 16 mm to about 18 mm in the flow direction from the proximal end 402 toward the distal end 404, compared to a landing zone of about 8 mm to about 10 mm for the cuff 112 of the prosthetic heart valve 100. Furthermore, the bellies of the leaflets 410 may be attached to the stent 406 and the cuff 412 a greater distance away from the proximal end 402 in the flow direction than the bellies of the leaflets 110 of the prosthetic heart valve 100. In one example, the belly of each of the leaflets 410 may be attached to the stent 406 and the cuff 412 a distance D1 of at least 10 mm from the proximal end 402 of the stent.

The prosthetic valve 400 having a cuff 412 with a relatively large landing zone may be used with any of the sealing rings disclosed herein. The large landing zone of the cuff 412 may permit a plurality of sealing rings to be attached thereto, the sealing rings being separated from one another in the flow direction (e.g., FIG. 5F).

FIGS. 5A-5F illustrate variants of sealing rings that may be used with prosthetic heart valves 300 or 300C in place of the sealing rings shown in FIGS. 3A-3C. Each of the sealing rings 550A-550F shown in FIGS. 5A-5F may be formed in the same manner, attached to the stent and cuff in the same manner, and made of the same material or materials described above with reference to the sealing rings 350A and 350C. Each of the sealing rings 550A-550F may be attached to a stent in any location along the longitudinal axis of the stent. A prosthetic heart valve, such as the prosthetic heart valve 300, may include one of the sealing rings 550A-550F, or alternatively, the prosthetic heart valve may include two or more of the sealing rings, as will be described in more detail below.

Figure 5A:
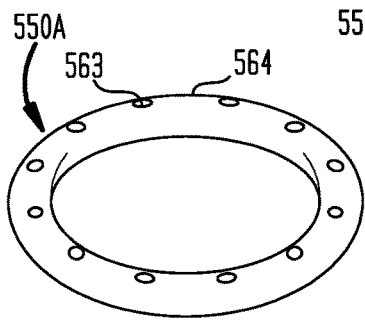
FIG. 5A is a highly schematic perspective view of an alternative sealing ring embodiment that can be used with the stent, cuff, and leaflets of FIG. 3A.
Figure 5B:
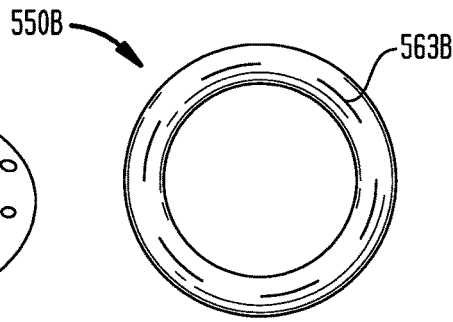
FIG. 5B is a highly schematic top view of an alternative sealing ring embodiment that can be used with the stent, cuff, and leaflets of FIG. 3A.

FIG. 5A shows a sealing ring 550A having a toroidal shape, similar to the toroidal-shaped sealing ring 350A shown in FIGS. 3A and 3B. The sealing ring 550A has openings 563 in a top surface 564 thereof. Any number of openings 563 may be provided in the sealing ring 550A, such as three, six, nine, twelve, fifteen, or eighteen, for example. The openings 563 may be round holes, as shown in FIG. 5A, or may be holes having any other shape or slits having any shape. For example, the sealing ring 550B shown in FIG. 5B has six openings 563B in the shape of oblong slits each extending partially around the sealing ring in a circumferential direction thereof. All of the other sealing rings described herein may include any number of openings in a top surface thereof, and such openings may be holes or slits having any shape.

The sealing ring 550A may be attached to a stent and cuff of a prosthetic heart valve in a similar manner as that described above with reference to the sealing ring 350A shown in FIGS. 3A and 3B. When the sealing ring 550A is attached to a stent and cuff of a prosthetic heart valve, the openings 563 and the top surface 564 will preferably face toward the distal end of the stent. When deployed in a patient, the openings 563 may allow the sealing ring 550A to fill with blood, which may augment the sealing ability of the sealing ring against the native aortic annulus or other native tissue structures. Instead of or in addition to the openings 563, the sealing ring 550A, and of all of the other sealing rings described herein, may include expanding materials within the interior of the sealing ring, such as polyacrylimide or other hydroscopic materials, PVA, shape memory foam, bovine gelatin or collagen, or the like.

Figure 5C:
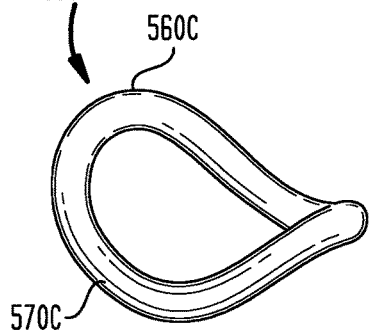
FIGS. 5C-5F are highly schematic perspective views of alternative sealing ring embodiments that can be used with the stent, cuff, and leaflets of FIG. 3A.

FIG. 5C shows a sealing ring 550C in the shape of a bent or saddle-shaped toroid that alternates between peaks 560C and valleys 570C around the circumference of the sealing ring, the peaks and valleys being substantially evenly distributed about the circumference. As shown in FIG. 5C, the sealing ring 550C has two peaks 560C and two valleys 570C, but the sealing ring may have other numbers of peaks and valleys, such as three, for example.

Figure 5D:
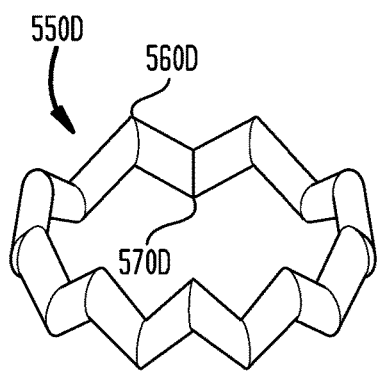

FIG. 5D shows a sealing ring 550D having a zigzag shape. The sealing ring 550D alternates between peaks 560D and valleys 570D around the circumference of the sealing ring, the peaks and valleys being substantially evenly distributed about the circumference. As shown in FIG. 5D, the sealing ring 550D has nine peaks 560D and nine valleys 570D, but the sealing ring may have other numbers of peaks and valleys, such as three or six, for example. A sealing ring having a zigzag shape may be stitched to the stent and the cuff along the struts. However, in other embodiments, the sealing ring 550D may be stitched to the stent and/or the cuff at other locations.

Figure 5E:
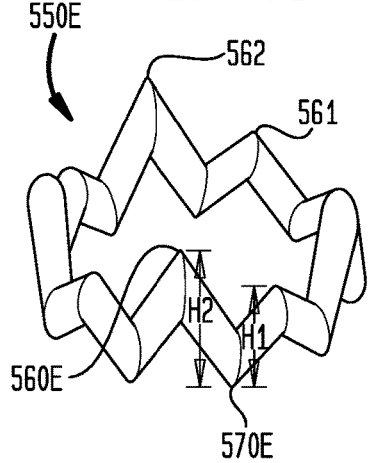

FIG. 5E shows a sealing ring 550E having a zigzag shape with alternating peak heights. The sealing ring 550E alternates between peaks 560E and valleys 570E around the circumference of the sealing ring, the peaks and valleys being substantially evenly distributed about the circumference. As shown in FIG. 5E, the sealing ring 550E has eight peaks 560E and eight valleys 570E, but the sealing ring may have other numbers of peaks and valleys, such as four or six, for example.

The peaks 560E include low peaks 561 that extend by a first height H1 above the valleys 570E and high peaks 562 that extend by a second height H2 above the valleys, the second height being greater than the first height. As shown in FIG. 5E, the peaks 560E may include four low peaks 561 and four high peaks 562, with one low peak separating adjacent ones of the high peaks. In other embodiments, there may be other numbers of high and low peaks. For example, a sealing ring having varying peak heights may include six low peaks and three high peaks, with two low peaks separating adjacent ones of the high peaks. In another example, a sealing ring having varying peak heights may include three low peaks and six high peaks, with two high peaks separating adjacent ones of the low peaks.

Such a configuration of a sealing ring having low peaks 561 and high peaks 562 at alternating heights may permit a smaller crimped diameter of the prosthetic heart valve when loaded into a delivery device. When the prosthetic heart valve is crimped into a delivery device, the low peaks 561 will be disposed at a different longitudinal location along the stent than the high peaks 562, thereby distributing the bulk of the peaks so that only half of the peaks are at any single longitudinal location.

Figure 5F:
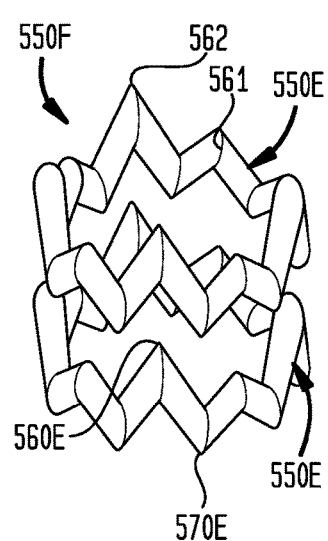

FIG. 5F shows a stacked arrangement of two sealing rings 550E each having a zigzag shape with alternating peak heights. As shown in FIG. 5F, the two sealing rings 550E are identical in structure and are aligned with one another such that the peaks 560E and valleys 570E of the upper sealing ring are substantially aligned longitudinally with the peaks and valleys of the lower sealing ring, and such that the low peaks 561 and high peaks 562 of the upper sealing ring are substantially aligned longitudinally with the low peaks and high peaks of the lower sealing ring, respectively. In other embodiments, the peaks 560E and valleys 570E of the two sealing rings 550E, and the low peaks 561 and the high peaks 562 of the two sealing rings need not be longitudinally aligned. In other embodiments, the two sealing rings need not have an identical structure.

Figure 5G:
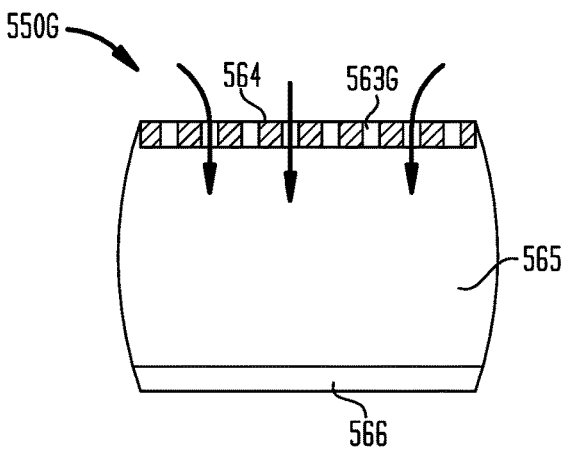
FIG. 5G is a highly schematic cross-sectional view of an alternative sealing ring embodiment that can be used with any of the sealing ring embodiments of FIGS. 5A-5F.

FIG. 5G illustrates a radial cross-section of a sealing ring 550G that may be incorporated into any of the sealing rings described herein. The sealing ring 550G shown in FIG. 5G may be formed in the same manner, attached to the stent and cuff in the same manner, and made of the same material or materials as described above with reference to the sealing rings 350A and 350C.

The top surface 564 of the sealing ring 550G may be made of a porous material having many small openings 563G that are adapted to allow unidirectional blood flow into the interior 565 of the sealing ring. The sealing ring 550G may have a bottom surface 566 without openings, and therefore may be substantially less permeable than the top surface 564. The bottom surface 566 may be made of a low-porosity material such as a tightly-woven fabric that may have a collagen or PVA coating, for example. The sealing ring 550G may be coated on the exterior of the top surface 564 and/or the bottom surface 566 with a material (e.g., Ag or a drug compound) to prevent a thrombus or infection from forming thereon.

As a result of this construction, the sealing ring 550G is adapted to allow blood to fill the interior 565 but not to escape. The porous material may be such that blood can only flow through the openings 563G into the interior 565 of the sealing ring when the pressure outside the sealing ring exceeds the pressure in the interior. When the pressure in the interior 565 equals or exceeds the pressure outside the sealing ring, the openings 563G will not permit blood to flow out of the interior.

Blood that flows into the interior 565 of the sealing ring 550G may coagulate and/or in-grow into the material of the sealing ring 550G, which may help provide stiffness to the sealing ring in a radial direction. To assist the blood to coagulate and/or in-grow, the openings 563G may be funneled so that the openings have a smaller diameter facing the interior 565 and a larger diameter at the top surface 564, and/or the material of the sealing ring 550G may be smooth on outside (e.g., on the top surface and/or the bottom surface 566) and rough on the surface facing the interior to provide a greater surface area of contact between the blood and the material of the sealing ring.

In one variation (not shown), the top surface 564 and the bottom surface 566 of the sealing ring 550G may be made of a porous material having many small openings that are adapted to allow blood flow into the interior 565 of the sealing ring. In this variation, before blood coagulation and/or in-growth, blood flowing into the openings 563G in the top surface 564 may be retained within the interior 565 because the native aortic annulus and/or native leaflets of the patient may at least partially block the openings in the bottom surface 566.

FIG. 6A illustrates a prosthetic heart valve 600 in accordance with another embodiment. As can be seen in FIG. 6A, the prosthetic heart valve 600 extends between a proximal end 602 and a distal end 604, and may generally include a stent 606 formed of a plurality of struts 607, and a valve assembly having a plurality of leaflets (not shown) and a cuff 612.

The prosthetic heart valve 600 further includes a generally flattened ring-shaped sealing ring 650A flattened in the flow direction of the stent 606, in contrast to the sealing ring 350A of FIGS. 3A and 3B, which is generally toroidal-shaped. Similar to the sealing ring 350A, the sealing ring 650A may be formed, for example, from a long, thin rectangle of material about 10 mm in width that is folded approximately in half longitudinally, and the opposed longitudinal edges may be stitched to one another to create a flattened tube about 5 mm in diameter. The sealing ring 650A may be annularly disposed around the abluminal surface of the stent 606 at the proximal end 602 of the prosthetic heart valve 600. The prosthetic heart valve 600 may include one of the sealing rings 650A, or alternatively, the prosthetic heart valve may include two or more of the sealing rings.

Alternatively, the sealing ring 650A may be made from a thin flat skirt cut from a strip or circle of porcine tissue without a seam. In one example, the circle of tissue comprising the sealing ring 650A may have an inner diameter D2 of about 29 mm, an outer diameter D3 of about 34 mm, and a width W1 between the inner diameter and the outer diameter of about 5 mm.

An inner edge 651 of the sealing ring 650A may be sutured to upper junctions 609B of the proximalmost struts 607 of the stent 606 to secure the sealing ring in place near the proximal end 602, using a running stitch, for example. An outer edge 652 of the sealing ring 650A may be a free edge that is not sutured to the stent 606 or the cuff 612. The outer edge 652 may be supported by a plurality of support members in the form of sutures 670 each extending between the outer edge and an upper junction 609D of certain struts 607 of the stent 606. Non-elastic or elastic sutures 670 may be used.

In one variation, sutures 670 may be used that shorten when heated, such that during loading of the prosthetic heart valve 600 into a delivery device, the sutures are long enough to permit the outer edge 652 of the sealing ring 650A to be pushed proximally away from the leaflets 610, to permit the valve to have a smaller crimped diameter. Then, when the prosthetic heart valve 600 is deployed into a patient, the heat from the patient may cause the sutures 670 to shorten, thereby pulling the outer edge 652 of the sealing ring 650A toward the position shown in FIG. 6A.

The sealing ring 650A may be configured such that when the prosthetic heart valve 600 is radially compressed within a delivery device, its top surface 664 folded up to confront the outer surface of the cuff 612. When the prosthetic heart valve 600 is released from the delivery device and deployed into a native aortic annulus, the sealing ring 650A may billow open when blood flows in a retrograde direction $D_R$ between the top surface 664 of the sealing ring and the outer surface of the cuff 612. The suture 670 can provide support to the outer edge 652 of the sealing ring 650A to prevent the sealing ring from opening beyond a position generally perpendicular to the cuff 612. When the sealing ring 650A is open to a position generally perpendicular to the cuff 612, the outer edge 652 of the sealing ring may extend up to about 5 mm radially outward from the stent 606, for example.

When the prosthetic heart valve 600 is deployed into a native aortic annulus, the blood flowing in the retrograde direction $D_R$ between the outer surface of the cuff 612 and the top surface 664 of the sealing ring may push the sealing ring 650A a greater radial distance away from the cuff at locations along the circumference of the sealing ring at which there is minimal radial force applied to the sealing ring from the native anatomy (i.e., at locations at which voids or gaps between the stent 606 and the native anatomy are present). The sealing ring 650A may expand a lesser radial distance at locations along the circumference of the sealing ring at which there is greater radial force applied to the sealing ring from the native anatomy (i.e., locations at which there are no such voids or gaps).

FIGS. 6B-6F illustrate prosthetic heart valve configurations that have embodiments of sealing rings that are variants of the sealing ring 650A shown in FIG. 6A, in which the sealing ring embodiments include stored energy elements in the form of springs that are configured to force portions of the outer edge of the sealing ring away from the cuff in locations at which voids or gaps between the stent 606 and the native anatomy are present.

Each of the sealing rings 650B-650F shown in FIGS. 6B-6F may be formed in the same manner, attached to the stent and cuff in the same manner, and made of the same material or materials described above with reference to the sealing ring 650A, with the exception of the addition of a stored energy element. Each of the sealing rings 650B-650F may be attached to the stent in any location along the longitudinal axis of the stent. A prosthetic heart valve, such as the prosthetic heart valve 600, may include one of the sealing rings 650B-650F, or alternatively, the prosthetic heart valve may include two or more of the sealing rings. Each of the sealing rings 650B-650F may be used with or without support members, such as the sutures 670 described above.

FIG. 6B shows a sealing ring 650B in the shape of a toroid similar to the toroidal-shaped sealing ring 650A shown in FIG. 6A. The sealing ring 650B has a plurality of stored energy elements in the form of springs 680B circumferentially spaced apart from one another about the sealing ring. Each spring 680B has a first end 681 located at the inner edge 651 of the sealing ring 650B and a second end 682 located at the outer edge 652. Each spring 680B preferably extends away from the inner edge 651 in a direction substantially perpendicular to the flow direction.

At least partially due to the capability of the springs 680B to store energy, the sealing ring 650B may have sufficient elasticity that it has a spring bias that tends to provide a force in a radially outward direction when the sealing ring is radially compressed. To provide this spring bias, each spring 680B may be made from a material having a shape memory, such as nitinol wire or spring steel. When a prosthetic heart valve having the sealing ring 650B is released from a delivery device, the second end 682 of each spring 680B preferably moves radially outward away from the cuff 612 according to its bias, thereby pushing the outer edge 652 of the sealing ring away from the cuff and the stent 606.

FIG. 6C shows a sealing ring 650C that is the same as the sealing ring 650B of FIG. 6B, except that the springs 680C preferably extend away from the inner edge 651 of the sealing ring such that all of the springs lie substantially in a plane that is perpendicular to the longitudinal axis of the prosthetic heart valve 600, with each spring 680C oriented at an acute angle with respect to the circumference of the stent 606. When viewed from the top surface 664 of the sealing ring 650C, as shown in FIG. 6C, the springs 680C may be oriented in a clockwise direction about the longitudinal axis of the sealing ring from their first end 681 to their second end 682. Alternatively, the springs 680C may be oriented in a counterclockwise direction about the longitudinal axis of the sealing ring from their first end 681 to their second end 682.

FIG. 6D shows a sealing ring 650D that is the same as the sealing ring 650B of FIG. 6B, except that the stored energy element is in the form of a coiled spring 680D that extends continuously about the circumference of the sealing ring or along substantial portions of the circumference of the sealing ring. To provide a radially-outward spring bias to the sealing ring 650D, the spring 680D may be made from a material having a shape memory, such as nitinol wire.

When a prosthetic heart valve having the sealing ring 650D is radially compressed inside a delivery device, the spring 680D will be under radial compression against its bias. When the prosthetic valve having the sealing ring 650D is released from the delivery device, the spring 680D will radially expand, such that the outer edge 652 of the sealing ring moves radially outward from the cuff 612 according to the bias of the spring.

FIG. 6E shows a sealing ring 650E that is the same as the sealing ring 650D of FIG. 6D, except that the stored energy element is in the form of a leaf spring 680E that extends in at least one complete loop about the circumference of the sealing ring, such that the first end 681 and the second end 682 of the spring each overlap another portion of the spring in the circumferential direction of the sealing ring. Similar to the sealing ring 650D, when a prosthetic valve having the sealing ring 650E is released from a delivery device, the spring 680E will radially expand, such that the outer edge 652 of the sealing ring moves radially outward from the cuff 612 according to the bias of the spring.

FIG. 6F shows a sealing ring 650F that is the same as the sealing ring 650E of FIG. 6E, except that the leaf spring 680F includes a ratchet element 683 that slidably couples either the first end 681 or the second end 682 of the spring to another portion of the spring. The ratchet element 683 is configured to allow the leaf spring to radially expand but not to radially contract. Similar to the sealing ring 650E, when a prosthetic valve having the sealing ring 650F is released from a delivery device, the spring 680F will radially expand, such that the outer edge 652 of the sealing ring moves radially outward from the cuff 612 according to the bias of the spring. Once the spring 680F has expanded, it will substantially maintain its diameter due to the ratchet element 683 preventing the spring from re-collapsing to a smaller radial profile.

FIG. 7A illustrates a heart valve 700A, which is a variant of the heart valve 600 of FIG. 6A. The heart valve 700A extends between a proximal end 702 and a distal end 704, and may generally include a stent 706 formed of struts 707, and a valve assembly having a plurality of leaflets (not shown) and a cuff 712. The heart valve 700A further includes a sealing ring 750A that is generally in the shape of a toroid flattened in the flow direction of the stent 706. The sealing ring 750A may be used with or without support members, such as the sutures 670 described above. In addition, the sealing ring 750A may be used with or without any energy storage elements, such as the springs 680B-680F described above.

Similar to the sealing ring 650A shown in FIG. 6A, the sealing ring 750A may be configured such that when the prosthetic heart valve 700 is radially compressed within a delivery device, the sealing ring extends distally from the location where it is attached to the cuff 712 and/or the stent 706, such that a top surface 764 of the sealing ring is folded up to confront the outer surface of the cuff 712. When the prosthetic heart valve 700A is released from the delivery device and deployed into a native aortic annulus, the sealing ring 750A may billow open when blood flows in a retrograde direction $D_R$ between the top surface 764 of the sealing ring and the outer surface of the cuff 712. When the sealing ring 750A is billowed open, it may flare outwardly and proximally from the cuff 712 in the flow direction of the prosthetic valve 700, so that the outer edge 752 is spaced apart from the cuff.

The sealing ring 750A may have sufficient rigidity that, when blood flows in a retrograde direction $D_R$ between the top surface 764 of the sealing ring and the outer surface of the cuff 712, the sealing ring will resist bending of the outer edge 752 too far away from the outer surface of the cuff, so that no portion of the top surface 764 opens beyond a perpendicular position relative to the cuff. To provide such a bending resistance, the sealing ring 750A may be reinforced with shape memory materials such as the springs 680B-680F described above, and/or the sealing ring may be made of a material that is elastic and/or has shape memory, so that when deployed, the sealing ring will be biased to take the shape shown in FIG. 7A. Also, to resist bending of the outer edge 752 too far away from the outer surface of the cuff, the outer edge of the sealing ring 750A may be sutured to certain ones of the struts 707. Non-elastic or elastic sutures may be used. In one variation, sutures that shorten when heated may be used.

After deployment into a patient, the sealing ring 750A may experience tissue ingrowth from the native tissue structures, which may help the sealing ring to resist bending when blood flows in the retrograde direction $D_R$ against the top surface 764 of the sealing ring. Also, the material of the sealing ring 750A may be configured so that certain areas therein have residual stress, so that when deployed, the sealing ring will be biased to take the shape shown in FIG. 7A.

To help provide the sealing ring 750A with the aforementioned rigidity, the sealing ring 750A may be sutured to the stent 706 at a location slightly spaced apart from the inner edge 751 of the sealing ring, so that the portion of the top surface 764 adjacent the inner edge is held substantially parallel to the outer surface of the cuff 712.

FIG. 7B shows a sealing ring 750B that is the same as the sealing ring 750A of FIG. 7A, except that the sealing ring 750B is oriented in the opposite direction. When the prosthetic heart valve 700B is radially compressed within a delivery device, the sealing ring 750B extends proximally from the location where it is attached to the cuff 712 and/or the stent 706, such that when the sealing ring 750B is billowed open, it may flare outwardly and distally from the cuff 712 in the flow direction of the prosthetic valve 700. The sealing ring 750B may be sutured to upper junctions 709B of the proximalmost struts 707 of the stent 706 at a location slightly spaced apart from the inner edge 751 of the sealing ring, so that the portion of the top surface 764 adjacent the inner edge is disposed substantially parallel to the outer surface of the cuff 712.

The outer edge 752 of the sealing ring 750B may extend below the proximal end 702 of the prosthetic heart valve 700B when the prosthetic heart valve 700B is in both its collapsed and expanded positions. Such a configuration may more evenly distribute the material of the leaflets and the sealing ring along the length of the prosthetic heart valve 700B, which may permit a smaller crimped diameter of the prosthetic heart valve when loaded into a delivery device.

Since the sealing ring 750B flares outwardly and distally from the cuff 712, blood flowing in a retrograde direction $D_R$ against the top surface 764 of the sealing ring may apply a radially inward force against the top surface that may tend to push the outer edge 752 of the sealing ring radially inward.

To counteract this radially inward force so that the sealing ring 750B maintains its outwardly flared shape along at least some portions of its circumference when deployed into a native annulus, the sealing ring may be used with energy storage elements, such as the springs 680B-680F described above, and/or the sealing ring may be made of a material that is elastic and/or has shape memory, so that when deployed, the sealing ring will be biased to take the shape shown in FIG. 7B.

Also, to counteract this radially inward force, the outer edge 752 of the sealing ring 750B may be sutured to certain ones of the struts 707. Non-elastic or elastic sutures may be used. In one variation, sutures that shorten when heated may be used, so that when deployed into a patient, the heat from the patient will shorten the sutures, thereby preventing the outer edge 752 from being pushed too far radially inward by blood flowing in a retrograde direction $D_R$ against the top surface 764 of the sealing ring.

Similar to the sealing ring 750A, after deployment into a patient, the sealing ring 750B may experience tissue ingrowth from the native tissue structures, which may help the sealing ring to resist bending when blood flows in the retrograde direction $D_R$ against the top surface 764 of the sealing ring. Also, the material of the sealing ring 750A may be configured so that certain areas therein have residual stress, so that when deployed, the sealing ring will be biased to take the shape shown in FIG. 7B.

FIG. 8A illustrates a portion of a prosthetic heart valve 800 according to an embodiment of the disclosure. The prosthetic heart valve 800 extends between a proximal end 802 and a distal end (not shown), and may generally include an expandable stent 806 formed of struts 807, and a valve assembly having a plurality of leaflets (not shown) and a cuff 812. Preferably, the cuff 812 has a relatively straight proximal end 811 at the proximal end 802 of the stent. In the illustrated embodiment, the cuff 812 is positioned on the luminal side of the stent 806 and is attached to the stent, for example, by sutures.

The prosthetic heart valve 800 includes an active sealing mechanism for sealing against a perivalvular leak in the form of one or more sealing members 820. In this example, the sealing members 820 take the form of parachute-like elements that billow open when blood flows in a retrograde direction $D_R$ into the parachute-like elements. If retrograde flow occurs on the abluminal side of prosthetic heart valve 800, the blood may enter one or more sealing members 820, causing the sealing members to billow open and facilitating the sealing of gap spaces between the patient's anatomy and the valve.

It should also be noted that, for this and other embodiments described herein, the sealing members 820 may help seal a gap space between the prosthetic valve 800 and the native anatomy even if there is little or no perivalvular leak to cause the sealing members to billow open. This may be due to, for example, the additional material of sealing members 820 filling gap spaces by virtue of the material being positioned in those gap spaces.

The sealing members 820 may take the form of generally triangular patches of material, although other shapes may be used (e.g., FIGS. 9A-10B). The sealing members 820 may be attached to the cuff 812 during valve assembly, or after valve assembly is otherwise complete. Any suitable attachment method, such as sewing, may be used. Preferably, a distal side 821 of each sealing member 820, in this case the distal side of the triangular patch, is left partially or completely unconnected to the cuff 806 while the other sides of the sealing member are connected to the cuff and/or stent so as to form a pocket open on one side.

For example, if sewing the triangular patch to the cuff 812 and/or the stent 806, two proximal sides 822, 823 of the triangle, meeting at a proximalmost point 824, are sewn to the cuff and/or struts 807, but the distal side 821 of the triangle facing the distal end 804 of the prosthetic heart valve 800 is not sewn to the cuff. With this configuration, the distal or open side 821 of sealing member 820 remains capable of widening upon retrograde blood flow, so that the pocket between the sealing member 820 and the cuff 812 fills with blood. As described above with reference to FIGS.

3A and 3B, at least some of the suturing used to attach the sealing members 820 to the struts 807 (and any of the other sealing members described herein) may be the same sutures that are used to attach the cuff 812 to the struts so that no extra steps or bulk is added.

The proximal sides 822, 823 of the sealing members 820 may be sewn to the cuff substantially along the contour of the struts 807. As shown in FIG. 8A, proximal sides 822, 823 are sewn to the cuff 812 along the contour of every strut of the bottom half of the first full row 813 of cells 815 between the proximalmost junctions 809A of the stent and the upper junctions 809B of the proximalmost struts 807 of the stent.

The closed proximal sides 822, 823 of the sealing members 820 that are connected to the cuff 812 may restrict blood from exiting the sealing members in the retrograde direction $D_R$. The proximal sides 822, 823 may be sewn such that the open sides 821 are loose or floppy, and not taught, thereby enabling blood to flow into sealing members 820. As described above, if retrograde blood flow does occur on the abluminal side of the prosthetic heart valve 800, the parachuting or billowing action of the sealing members 820 upon blood flowing therein facilitates active sealing between the prosthetic heart valve and the native tissue surrounding the valve.

In a variation that may be applied to any of the embodiments of the sealing members described herein (e.g., any of the sealing members of FIGS. 8A through 10B), another design that may restrict blood flow from exiting the sealing members may have one or more portions of the open sides 821 of the sealing members 820 stitched (or joined in another way) to the cuff 812 and/or the stent 806. For example, the left and right peripheral quarters of the length of the open sides 821 may be stitched to the cuff 812, while the center half of the length of the open sides may remain unconnected to the cuff. In another example, one of the left or right halves of the length of the open sides 821 may be stitched to the cuff 812, while the other half may remain unconnected to the cuff.

Such a variation may improve the ability of the sealing members 820 to retain blood therein without expelling emboli. Although this variation has been described above as having half of the length of the open side 821 stitched to the cuff 812 and half of the length unconnected to the cuff, that need not be the case. In other variations, any portion or portions of the open side 821 of the sealing members 820 may be attached to the cuff 812 and/or the stent 806, and any remaining portion of the open side may remain unconnected to the cuff and/or stent.

FIGS. 8B and 8C show prosthetic heart valves 800B and 800C that are variants of the prosthetic heart valve 800 of FIG. 8A. Compared to the prosthetic heart valve 800 of FIG. 8A, the prosthetic heart valves 800B and 800C may reduce the volume of the material of the sealing members, which may permit a smaller crimped diameter of the prosthetic heart valve when loaded into a delivery device, and therefore may reduce the force required to load the prosthetic heart valve into a delivery device and to perform any resheathing procedure.

Referring to FIG. 8B, rather than having a sealing member disposed in every open cell 815 of the first row of cells 813 of the stent 806, the prosthetic heart valve 800B may have three narrow sealing members 820B that are the same as the sealing members 820 of FIG. 8A and three wide sealing members 825B that each extend in a circumferential direction across two cells. Each of the wide sealing members 825B may be substantially aligned in the flow direction with a commissure feature 866, and each of the narrow sealing members 820B may be substantially aligned in the flow direction with the lowest positions 811 at which the bellies of the leaflets 810 attach to the cuff 812.

Referring to FIG. 8C, the prosthetic heart valve 800C may have one narrow sealing member 820C that is the same as the sealing members 820 of FIG. 8A and four wide sealing members 825C that each extend in a circumferential direction across two cells. Two of the wide sealing members 825C may be substantially aligned in the flow direction with a commissure feature 866, while the other two wide sealing members may be aligned in the flow direction between a commissure feature and the lowest positions 811 at which the bellies of the leaflets 810 attach to the cuff 812. The narrow sealing member 820C may be aligned in the flow direction with the lowest position 811 at which the belly of one of the leaflets 810 attaches to the cuff 812.

FIGS. 9A-9D show prosthetic heart valves 900A-900D that are variants of the prosthetic heart valve 800 of FIG. 8A. Compared to the prosthetic heart valve 800 of FIG. 8A, the prosthetic heart valves 900A-900D may reduce the volume of the material of the sealing members, which may permit a smaller crimped diameter of the prosthetic heart valve when loaded into a delivery device, and therefore may reduce the force required to load the prosthetic heart valve into a delivery device and to perform any resheathing procedure.

Referring to FIG. 9A, the prosthetic heart valve 900A is the same as the prosthetic heart valve 800C of FIG. 8C, except that the wide sealing members 925A and the narrow sealing member 920A are crescent shaped rather than triangular shaped, and each crescent extends only a portion of the longitudinal distance from the upper junctions 909B of the proximalmost struts 907 of the stent 906 proximally toward the proximalmost junctions 909A of the stent. Each sealing member 920A and 925A may have a distal or open side 921 facing the distal end 904 of the stent 906 that is not sewn to the cuff, and a proximal or closed side 922 facing the proximal end 902 of the stent that is sewn to the cuff.

Referring to FIG. 9B, the prosthetic heart valve 900B is the same as the prosthetic heart valve 800B of FIG. 8B, except that the wide sealing members 925B and the narrow sealing members 920B are crescent shaped rather than triangular shaped, and each crescent extends only a portion of the longitudinal distance from the upper junctions 909B of the proximalmost struts 907 of the stent 906 proximally toward the proximalmost junctions 909A of the stent. Each sealing member 920B and 925B may have a distal or open side 921 facing the distal end 904 of the stent 906 that is not sewn to the cuff, and a proximal or closed side 922 facing the proximal end 902 of the stent that is sewn to the cuff.

Referring to FIG. 9C, the prosthetic heart valve 900C is the same as the prosthetic heart valve 900A of FIG. 9A, except that the wide sealing members 925C each extend in the circumferential direction across three cells of the stent 906, and the narrow sealing members are omitted. The wide sealing members 925C each extend in the flow direction approximately between the upper junctions 909C of certain cells in a first full row 913 of complete cells 915 and upper junctions 909B of the proximalmost struts 907 of the stent. Each of the wide sealing members 925C is substantially aligned in the flow direction with a commissure feature 966.

FIG. 9D shows a prosthetic heart valve 900D that is a variant of the prosthetic heart valve 900C of FIG. 9C. The prosthetic heart valve 900D has six wide crescent-shaped sealing members each extending circumferentially across two cells, the sealing members being located at two different heights in the flow direction of the stent 906.

The prosthetic heart valve 900D has three lower sealing members 925D that have the same shape as the wide sealing members 925A of FIG. 9A. Each of the lower sealing members 925D extends across a portion of the longitudinal distance from the upper junctions 909B of the proximalmost struts 907 of the stent 906 proximally toward the proximalmost junctions 909A of the stent, and is substantially aligned in the flow direction with a commissure feature 966.

The prosthetic heart valve 900D also has three upper sealing members 926D that have the same shape as the sealing members 925D. Each of the upper sealing members 926D extends across a portion of the longitudinal distance from the upper junctions 909C of certain cells in a first full row 913 of complete cells 915 and upper junctions 909B of the proximalmost struts 907 of the stent 906. Each of the upper sealing members 926D is substantially aligned in the flow direction with the lowest positions 911 at which the bellies of the leaflets 910 attach to the cuff 912.

Each lower sealing member 925D overlies two upper sealing members 926D in the flow direction of the stent 906, while each upper sealing member 926D overlies two lower sealing members 925D in the flow direction of the stent. It is preferred that the lower sealing members 925D and the upper sealing members 926D be attached to a cuff having a higher cuff height in the flow direction of the stent 906, such as the cuff 412 of FIG. 4.

FIGS. 10A and 10B illustrate a prosthetic heart valve 1000 in accordance with another embodiment. As can be seen in FIGS. 10A and 10B, the prosthetic heart valve 1000 extends between a proximal end 1002 and a distal end 1004, and may generally include a stent 1006 formed of a plurality of struts 1007, and a valve assembly 1008 having a plurality of leaflets 1010 and a cuff 1012. Preferably, the cuff 1012 has a relatively straight proximal end 1011 at the proximal end 1002 of the stent.

The prosthetic heart valve 1000 further includes nine independent sealing members 1020 that may take the form of generally rectangular patches of material, although other shapes may be used. Preferably, a distal side 1021 of each sealing member 1020 is left partially or completely unconnected to the cuff 1012, and a proximal side 1022 is sewn to the proximal end 1011 of the cuff. With this configuration, the distal or open sides 1021 of the sealing members 1020 are capable of opening upon retrograde blood flow, with the open side facing the distal end 1004 of the prosthetic heart valve 1000.

Each sealing member 1020 may independently billow radially outward by a different amount, depending on the contour of the adjacent native anatomy. The sealing members 1020 may be used with support members, such as the sutures 670 described above, in order to limit the outward billowing of the sealing members. In addition, the sealing members 1020 may be used with energy storage elements, such as the plurality of springs 680B-680C described above, with one spring 680B or 680C attached to each sealing member 1020, for example, so that the outer edge 1052 of one or more sealing members may be forced away from the cuff 1012 in locations at which voids or gaps between the stent 1006 and the native anatomy are present.

Furthermore, the sealing members 1020 may be configured to flare outwardly and proximally from the cuff 1012 in the flow direction of the prosthetic valve 1000 in a manner similar to the sealing rings 750A or 750B. The sealing members 1020 may have sufficient rigidity to resist bending of the outer edge 1052 too far away from the outer surface of the cuff 1012 when retrograde blood flow extends between the sealing members and the outer surface of the cuff, so that no portion of the top surface 1064 opens beyond a perpendicular position relative to the cuff.

Although some of the various sealing structures have been described herein as "sealing rings," it is to be understood that the term "sealing ring" as used herein may describe one or more discontinuous sealing structures that do not completely extend around the circumference of the stent of a prosthetic heart valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve configured to be expanded in an annulus of a native aortic valve of a patient, the prosthetic heart valve comprising:
    a stent extending in a flow direction from an inflow end to an outflow end, the stent having an expanded condition and a collapsed condition and including an annulus section adjacent to the inflow end and a plurality of struts shaped to form a plurality of cells connected to one another in a plurality of annular rows around the stent, the plurality of annular rows of cells including a first full row of cells at the inflow end of the stent, each cell in the first full row of cells being diamond-shaped and having two proximalmost struts, the proximalmost struts of each cell in the first full row of cells meeting at a proximalmost junction of the stent, pairs of adjacent ones of the proximalmost struts meeting at respective upper junctions;
    a cuff attached to the annulus section of the stent and having an outer surface facing in radial directions orthogonal to the flow direction, the cuff having a straight proximal end;
    a plurality of prosthetic valve leaflets attached to the cuff; and
    at least one sealing member comprising (i) a first proximal side, whereby one or more sutures attach the first proximal side to a first one of the two proximalmost struts of a respective cell in the first full row of cells, (ii) a second proximal side, whereby one or more sutures attach the second proximal side to a second one of the two proximalmost struts of the respective cell in the first full row of cells, and (iii) a distal side unconnected to the cuff;
    wherein in the expanded condition of the prosthetic heart valve, the at least one sealing member forms a pocket between the sealing member and the cuff.

2. The prosthetic heart valve of claim 1, wherein the at least one sealing member billows radially outward when retrograde blood flow occurs on an abluminal side of the prosthetic heart valve when the prosthetic heart valve is expanded in the annulus of the native aortic valve of the patient.

3. The prosthetic heart valve as claimed in claim 1, wherein the proximal end of the cuff is attached to the stent by cuff sutures, and the first and second proximal sides of the at least one sealing member are attached to the proximal end of the cuff by the cuff sutures.

4. The prosthetic heart valve of claim 1, wherein the first and second proximal sides of the at least one sealing member is are sewn to the cuff substantially along a contour of one or more struts at the inflow end of the stent.

5. The prosthetic heart valve of claim 1, wherein the at least one sealing member is annularly disposed around an abluminal surface of the stent at the inflow end of the prosthetic heart valve.

6. The prosthetic heart valve of claim 1, wherein the at least one sealing member extends completely around a circumference of the stent.

7. The prosthetic heart valve of claim 1, wherein the at least one sealing member is formed from a triangular patch of material.

8. The prosthetic heart valve of claim 1, wherein
each leaflet is attached to the cuff along a belly portion, the belly portion including an attachment point at which the leaflet is closest to the inflow end of the stent,
each of the attachment points is at a predetermined distance from the inflow end of the stent,
the attachment points collectively define a positioning line circumscribing a circumference of the stent at the predetermined distance from the inflow end of the stent, and
the distal side of the at least one sealing member is located between the outflow end of the stent and the positioning line.

9. A prosthetic heart valve configured to be expanded in an annulus of a native aortic valve of a patient, the prosthetic heart valve comprising:
a stent extending in a flow direction from an inflow end to an outflow end, the stent having an expanded condition and a collapsed condition and including an annulus section adjacent to the inflow end and a plurality of struts shaped to form a plurality of cells connected to one another in a plurality of annular rows around the stent, the plurality of annular rows of cells including a first full row of cells at the inflow end of the stent, each cell in the first full row of cells being diamond-shaped and having two proximalmost struts, the proximalmost struts of each cell in the first full row of cells meeting at a proximalmost junction of the stent, pairs of adjacent ones of the proximalmost struts meeting at respective upper junctions;
a cuff attached to the annulus section of the stent and having an outer surface facing in radial directions orthogonal to the flow direction, the cuff having a straight proximal end;
a plurality of prosthetic valve leaflets attached to the cuff; and
an active sealing mechanism for sealing against a perivalvular leak, the active sealing mechanism comprising at least one sealing member, the active sealing mechanism comprising (i) a first proximal side, whereby one or more sutures attach the first proximal side to a first one of the two proximalmost struts of a respective cell in the first full row of cells, (ii) a second proximal side, whereby one or more sutures attach the second proximal side to a second one of the two proximalmost struts of the respective cell in the first full row of cells, and (iii) a distal side unconnected to the cuff;
wherein in the expanded condition of the prosthetic heart valve, the at least one sealing member forms a pocket between the sealing member and the cuff.

10. The prosthetic heart valve of claim 9, wherein the active sealing mechanism billows radially outward when retrograde blood flow occurs on an abluminal side of the prosthetic heart valve when the prosthetic heart valve is expanded in the annulus of the native aortic valve of the patient.

11. The prosthetic heart valve as claimed in claim 9, wherein the proximal end of the cuff is attached to the stent by cuff sutures, and the first and second proximal sides of the active sealing mechanism are attached to the proximal end of the cuff by the cuff sutures.

12. The prosthetic heart valve of claim 9, wherein the first and second proximal sides of the active sealing mechanism are sewn to the cuff substantially along a contour of one or more struts at the inflow end of the stent.

13. The prosthetic heart valve of claim 9, wherein the active sealing mechanism is annularly disposed around an abluminal surface of the stent at the inflow end of the prosthetic heart valve.

14. The prosthetic heart valve of claim 9, wherein the active sealing mechanism extends completely around a circumference of the stent.

15. The prosthetic heart valve of claim 9, wherein the active sealing mechanism is formed from a triangular patch of material.

16. The prosthetic heart valve of claim 9, wherein
each leaflet is attached to the cuff along a belly portion, the belly portion including an attachment point at which the leaflet is closest to the inflow end of the stent,
each of the attachment points is at a predetermined distance from the inflow end of the stent,
the attachment points collectively define a positioning line circumscribing a circumference of the stent at the predetermined distance from the inflow end of the stent, and
the distal side of the active sealing mechanism is located between the outflow end of the stent and the positioning line.

17. A prosthetic heart valve configured to be expanded in an annulus of a native aortic valve of a patient, the prosthetic heart valve comprising:
a stent extending in a flow direction from an inflow end to an outflow end, the stent having an expanded condition and a collapsed condition and including an annulus section adjacent to the inflow end and a plurality of struts shaped to form a plurality of cells connected to one another in a plurality of annular rows around the stent, the plurality of annular rows of cells including a first full row of cells at the inflow end of the stent, each cell in the first full row of cells being diamond-shaped and having two proximalmost struts, the proximalmost struts of each cell in the first full row of cells meeting at a proximalmost junction of the stent, pairs of adjacent ones of the proximalmost struts meeting at respective upper junctions;
a cuff attached to the annulus section of the stent and having an outer surface facing in radial directions orthogonal to the flow direction, the cuff having a straight proximal end;
a plurality of prosthetic valve leaflets attached to the cuff; and
a sealing structure extending continuously around a circumference of the stent, the sealing structure comprising at least one sealing member comprising (i) a first proximal side, whereby one or more sutures attach the first proximal side to a first one of the two proximalmost struts of a respective cell in the first full row of cells, (ii) a second proximal side, whereby one or more sutures attach the second proximal side to a second one of the two proximalmost struts of the respective cell in the first full row of cells, and (iii) a distal side unconnected to the cuff;

wherein in the expanded condition of the prosthetic heart valve, the at least one sealing member forms a pocket between the sealing member and the cuff.

18. The prosthetic heart valve of claim 17, wherein the sealing structure billows radially outward when retrograde blood flow occurs on an abluminal side of the prosthetic heart valve when the prosthetic heart valve is expanded in the annulus of the native aortic valve of the patient.

19. The prosthetic heart valve of claim 17, wherein the sealing structure is annularly disposed around an abluminal surface of the stent at the inflow end of the prosthetic heart valve.

* * * * *